US006935165B2

(12) United States Patent
Bashir et al.

(10) Patent No.: US 6,935,165 B2
(45) Date of Patent: Aug. 30, 2005

(54) MICROSCALE SENSOR ELEMENT AND RELATED DEVICE AND METHOD OF USE

(75) Inventors: Rashid Bashir, West Lafeyette, IN (US); Nicholas A. Peppas, Austin, TX (US); James Z. Hilt, Austin, TX (US); Amit K. Gupta, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/389,023

(22) Filed: Jun. 24, 2003

(65) Prior Publication Data

US 2004/0007051 A1 Jan. 15, 2004

Related U.S. Application Data

(60) Provisional application No. 60/366,324, filed on Mar. 20, 2002.

(51) Int. Cl.[7] ............................................. G01N 29/00
(52) U.S. Cl. ...................................... 73/64.53; 73/61.75
(58) Field of Search ........................... 73/64.53, 61.75, 73/24.01, 24.03, 24.06, 863.71, 863.72, 863.73

(56) References Cited

U.S. PATENT DOCUMENTS

| | | | | |
|---|---|---|---|---|
| 4,848,139 A | * | 7/1989 | Blake-Coleman et al. | 73/61.75 |
| 4,909,065 A | * | 3/1990 | Barney | 73/19.05 |
| 5,028,394 A | * | 7/1991 | Lowell et al. | 422/58 |
| 5,212,988 A | * | 5/1993 | White et al. | 73/599 |
| 5,456,114 A | * | 10/1995 | Liu et al. | 73/597 |
| 5,644,395 A | * | 7/1997 | Folta | 356/246 |
| 6,399,303 B1 | * | 6/2002 | Connolly | 435/6 |
| 2003/0222232 | * | 12/2003 | Welland et al. | 250/573 |
| 2004/0023413 | * | 2/2004 | Opalsky | 436/518 |

OTHER PUBLICATIONS

U.S. Appl. No. 60/333,591.*

* cited by examiner

*Primary Examiner*—Michael Cygan
(74) *Attorney, Agent, or Firm*—F. Neil Sudol; Henry D. Coleman; William J. Sapone

(57) ABSTRACT

A monitoring apparatus useful in detecting viability of biological cells. A substrate defines a microscopic chamber. One or more microcantilevers extend from the substrate into the chamber. A detector is operatively connected to the microcantilevers for sensing a state of deformation thereof. On each microcantilevers is deposited a layer of an environmentally sensitive hydrogel polymer having a configuration changing in accordance with presence of an environmental parameter.

29 Claims, 27 Drawing Sheets

A)

B)

US 6,935,165 B2

MICROSCALE SENSOR ELEMENT AND RELATED DEVICE AND METHOD OF USE

CROSS REFERENCE TO RELATED APPLICATION

This application claims priority from provisional application No. 60/366,324, filed on Mar. 20, 2002.

STATEMENT REGARDING FEDERALLY SPONSORED RESEARCH

This invention was made in part with government support under grant numbers DGE-99-72770 and ECS-99-84199 awarded by the National Science Foundation. The Government has certain rights in the invention.

FIELD OF THE INVENTION

The invention relates to a microscale sensor. More particularly, this invention relates to a microscale sensor or microsensor of a cantilever type. This invention also relates to a sensing device incorporating the sensing element and to an associated method using the device. This invention additionally relates to a method of manufacturing the microscale cantilever-type sensor.

BACKGROUND OF THE INVENTION

A cantilever is a projecting structure that is supported at only one end. Macroscopic cantilevers have been used to monitor surface stresses for over 30 years. For instance, several groups have utilized macroscale cantilevers to monitor stress development in ultraviolet-cured polymer coatings [Wen, M., L. E. Scriven, and A. V. McCormick. Differential scanning calorimetry and cantilever deflection studies of polymerization kinetics and stress in ultraviolet curing of multifunctional (meth)acrylate coatings. Macromolecules, 35, 112–120 (2002); Payne, J. A., L. F. Francis, and A. V. McCormick. The effects of processing variables on stress development in ultraviolet-cured coatings. J. Appl. Polym. Sci., 66, 1267–1277 (1997); Lange, J., S. Toll, J. E. Manson, and A. Hult. Residual stress build-up in thermoset films cured above their ultimate glass transition temperature. Polymer, 36, 3135–3141 (1995)]. In these applications, the surface stress differences measured are on the order of a few mPa. Microcantilevers are used for measurement of deflections resulting from small surface stress changes or surface mass changes due to adsorption of molecules.

Since the invention of the atomic force microscope (AFM), microcantilevers have been utilized as ultra-sensitive force sensors in AFM systems. In the early 1990's, researchers demonstrated that they were able to measure molecular forces, such as avidin-biotin binding [Florin, E. L., V. T. Moy, and H. E. Gaub. Adhesion forces between individual ligand-receptor pairs. Science, 264, 415–417 (1994)], antigen-antibody interaction [Hinterdorfer, P., W. Baumgartner, H. J. Gruber, K. Schilcher, and H. Schindler. Detection and localization of individual antibody-antigen recognition events by atomic force microscopy. Proc. Natl. Acad. Sci. U.S.A., 93, 3477–3481 (1996)], and hybridization of complementary DNA strands interactions [Lee, G. U., L. A. Chrisey, and R. J. Colton. Direct measurement of the forces between complementary strands of DNA. Science, 266, 771–773 (1994)] using AFM systems. These remarkable accomplishments resulted in many groups focusing research on developing microsensors based on the silicon microcantilevers that are responsible for this tremendous sensitivity.

Microcantilever Detection Methods

The two common methods of measuring the response of a microcantilever are determination of bending of the beam and measurement of a change in the resonance frequency. Both of these detection methods are achieved with either optical or electrical methods. The most common detection method is to use the beam bounce or optical lever technique based on an AFM set-up [Raiteri R., M. Grattarola, H. Butt, and P. Skladal. Micromechanical cantilever-based biosensors. Sensors and Actuators B, 79, 115–126 (2001)]. For this method, depicted in FIG. 1, a low power laser diode 20 is utilized to project a visible light beam 22 onto the end of a cantilever 24. A reflected beam 26 emanating from the cantilever surface at an angle $\phi$ with respect to the incident beam 22 is captured in a photodetector 28. With the deflection or vibration of the cantilever 24, the light is reflected to a different degree and strikes the photodetector or photodiode 28 at a different position on its surface.

Another useful detection method is based on piezoresistors. When a piezoresistive material, such as doped silicon, is strained, the resistance of the material changes. Piezoresistors can be integrated into microcantilevers by dopant implantation into the silicon at the cantilever's base. Then, the cantilever's bending or vibration initiates strain in this piezoresistor that leads to a change in its electrical conductivity, and this conductance can be easily monitored with simple circuitry. The governing equation for piezoresistance is the following [Madou, M. J., Fundamentals of Microfabrication. CRC Press, Boca Raton, Fla., 1997]:

$$\frac{\Delta R}{R} = \sigma_l \pi_l + \sigma_t \pi_t \quad (2.1)$$

Here, R is the resistance, $\sigma_l$ is the longitudinal stress component (stress component parallel to the direction of the current), $\sigma_t$ is the transversal stress component (the stress component perpendicular to the direction of current), $\pi_l$ is the longitudinal piezoresistance coefficient, and $\pi_t$ is the transversal piezoresistance coefficient. The piezoresistance coefficients are functions of the material and, additionally, the crystal orientation within the material. Although the fabrication of a piezoresistive cantilever is more complex, the piezoresistive detection results in several advantages relative to optical detection. For example, there is no need for external optical components, detection is done on chip, and the read-out microelectronics can easily be integrated on the silicon chip.

Detection in a microcantilever sensor can be attained by observing the bending of the cantilever beam. The governing relationship for cantilever bending is given by the Stoney's equation:

$$\Delta h = \frac{3L^2(1-\nu)}{E\delta^2}(\sigma_1 - \sigma_2) \quad 2.2$$

[Moulin, A. M., S. J. O'Shea, and M. E. Welland. Microcantilever-based biosensors. Ultramicroscopy, 82, 23–31 (2000)]. Here, $(\sigma_1-\sigma_2)$ is the difference in the surface stress between the two opposing sides of the cantilever, E is the Young's modulus of the cantilever, $\nu$ is the Poisson ratio, $\delta$ is the thickness, L is the length, and $\Delta h$ is the deflection of the end of the cantilever. From this relation, it can be seen that the deflection of the cantilever is amplified by increasing the length and decreasing the thickness. Through the use of optical detection methods, microcantilever deflections have been detected with an amazing resolution of 400 fm at room temperature [Varesi, J., J. Lai, T. Perazzo, Z. Shi, and A. Majumdar. Photothermal measurements at picowatt resolution using uncooled micro-optomechanical sensors. Appl. Phys. Lett., 71, 306–308 (1997)].

When used in the resonant sensor mode, the resonance frequency can be monitored, or additional parameters, such as the vibration amplitude, the phase, or the quality factor of the resonance. The resonance frequency dependence on a change in mass can be expressed as:

$$\Delta f = 0.279 m_{eff} \sqrt{\frac{EI}{l^3 m_o^3}} \quad (2.3)$$

[Ilic B., D. Czaplewski, M. Zalalutdinov, H. G. Craighead, P. Neuzil, C. Campagnolo, and C. Batt. Single cell detection with micromechanical oscillators. J. Vac. Sci. Technol. B., 19, 2825–2828 (2001)]. Here, $\Delta f$ is the change in resonance frequency, $m_{eff}$ is the effective mass of the loaded cantilever, $m_o$ is the initial mass of the cantilever, E is the Young's modulus for the cantilever, I is the moment of inertia of the cantilever, and l is the length of the cantilever. Therefore, the larger the loaded mass, the larger the change in the resonance frequency will be. This technique has been used to achieve extreme sensitivities on the order of a change of 10 Hz/fg allowing for masses on the order of a fg to be easily detected. [Ilic B., D. Czaplewski, M. Zalalutdinov, H. G. Craighead, P. Neuzil, C. Campagnolo, and C. Batt. Single cell detection with micromechanical oscillators. J. Vac. Sci. Technol. B., 19, 2825–2828 (2001).] This ultrasensitivity of microcantilevers has led to their application in numerous sensor applications.

Microcantilevers in Sensors

Extensive research has been focused on designing and fabricating microsensors based on the ultrasensitive detection abilities of microcantilevers that were described above. For integration as microsensors, the surface of the microcantilever needs to be functionalized. The methods for functionalization of the microcantilever surface include treatment with self-assembled monolayers (SAMs), coating with polymers, coating with metals, and adsorption of receptor molecules.

Self-assembled monolayers (SAMs) are ordered molecular assemblies that spontaneously form by the adsorption of a surfactant with a specific affinity of its head group to a substrate [Schreiber, F. Structure and growth of self-assembling monolayers. Progress in Surface Science, 65, 151–256 (2000)]. The head and tail groups can be tailored to modify a surface in a specific way. The SAMs systems that have received the most attention are organosilane species ($RSiX_3$, $R_2SiX_2$, or $R_3SiX$, where R is an alkyl chain and X is a chloro or alkoxy group) on a hydroxylated substrate, such as glass, silicon dioxide, and aluminum oxide; and organosulfur species (for example, alkanethiols) on a noble metal surface, such as gold. The versatility of surface modification via SAMs has led to the application of SAMs in a number of areas, including for immobilization of biological components such as oligonucleotides, proteins, antibodies, and receptors for application in biosensors [Wink, T., S. J. van Zuilen, A. Bult, and W. P. van Bennekom. Self-assembled monolayers for biosensors. Analyst, 122, 43R–50R (1997)]; adhesion promoters for biological applications [Ohashi, K. L., S. A. Yerby, and R. H. Dauskardt. Effects of an adhesion promoter on the debond resistance of a metal-polymethylmethacrylate interface. J. Biomed. Mater. Res., 54, 419–427 (2001); Wang, M. and W. Bonfield. Chemically coupled hydroxyapatite-polyethylene composites: structure and properties. Biomaterials, 22, 1311–1320 (2001)]; adhesion promoters for other applications [Plueddemann, E. P. Silane Coupling Agents, 2nd Edition. Plenum Press, New York, 1991]; and ultrathin resists [Xia, Y., X. Zhao, and G. M. Whitesides. Pattern transfer: Self-assembled monolayers as ultrathin resists. Microelectronic Engineering, 32, 255–268 (1996)]. Of specific interest within is the application of SAMs as both surface modifiers for application in sensors and as adhesion promoters for bonding organic and inorganic materials.

Several groups have utilized SAMs to functionalize microcantilevers for sensing applications. In work by Majumdar's and Thundat's groups, a microcantilever-based optical deflection assay based on gold-coated silicon AFM cantilevers functionalized with thiolated DNA oligonucleotides was successfully used to discriminate between DNA single-nucleotide mismatches. [Wu G., H. Ji, K. Hansen, T. Thundat, R. Datar, R. Cote, M. F. Cote, M. F. Hagan, A. K. Chakraborty, and A. Majumdar. Origin of nanomechanical cantilever motion generated from biomolecular interactions. Proc. Natl. Acad. Sci. U.S.A., 98, 1560–1564 (2001); Hansen, K. M., H. Ji, G. Wu, R. Datar, R. Cote, A. Majumdar, and T. Thundat. Cantilever-based optical deflection assay for discrimination of DNA single-nucleotide mismatches. Anal. Chem., 73, 1567–1571 (2001).] In other work by Thundat's group, surface modified silicon dioxide and silicon nitride microcantilevers were utilized to precisely detect pH changes. [Ji, H., K. M. Hansen, Z. Hu, and T. Thundat. Detection of pH variation using modified microcantilever sensors. Sensors and Actuators B, 72, 233–238 (2001).] In other work, Fritz et al. observed the nanomechanical response of microcantilevers, via surface stress changes, as a result of DNA hybridization and receptor-ligand binding. For this, cantilevers in arrays were functionalized by immobilizing SAMs of receptor molecules, and then bending was monitored in a liquid environment. [Fritz, J., M. K. Baller, H. P. Lang, H. Rothuizen, P. Vettiger, E. Meyer, H. J. Guntherodt, C. Gerber, J. K. Gimzewski. Translating biomolecular recognition into nanomechanics. Science, 288, 316–318 (2000).] In related work, Moulin et al. functionalized commercial microcantilevers to create biosensors and the deflection was measured using a standard AFM set-up. The analytes targeted were lipoproteins and their oxidized form, which are responsible for cholesterol accumulation in arteries. [Moulin, A. M., S. J. O'Shea, and M. E. Welland. Microcantilever-based biosensors. Ultramicroscopy, 82, 23–31 (2000).] Lavrik et al. developed a process of coating microcantilevers with gold nanospheres modified with SAMs that dramatically increased the deflection sensitivity to chemical stimuli. [Lavrik, N. V., C. A. Tipple, M. J. Sepaniak, and P. G. Datskos. Enhanced chemimechanical transduction at nanostructured interfaces. Chemical Physics Letters, 336, 371–376 (2001); Lavrik, N. V., C. A. Tipple, M. J. Sepaniak, and P. G. Datskos. Gold nano-structures for transduction of biomolecular interactions into micrometer scale movements. Biomedical Microdevices, 3, 35–44 (2001).]

Several other groups have focused on utilizing polymer coatings to functionalize microcantilevers for application in microsensors. Guntherodt and others have developed an artificial nose based on an array of eight cantilevers that had been coated with different polymers. [Baller, M. K., H. P. Lang, J. Fritz, C. Gerber, J. K. Gimzewski, U. Drechsler, H. Rothuizen, M. Despont, P. Vettiger, F. M. Battiston, J. P. Ramseyer, P. Fomaro, E. Meyer, and H. J. Guntherodt. A cantilever array-based artificial nose. Ultramicroscopy, 82, 1–9 (2000); Battiston, F. M., J. P. Ramseyer, H. P. Lang, M. K. Baller, C. Gerber, J. K. Gimzewski, E. Meyer, H. J. Guntherodt. A chemical sensor based on a microfabricated cantilever array with simultaneous resonance-frequency and bending readout. Sensors and Actuators B, 77, 122–131 (2001).] The fingerprint of an analyte was achieved by detecting the varying deflections and resonance frequency changes of the cantilevers in the array using optical detection. In other work, polymers have been coated onto piezoresistive microcantilevers to create a sensor for various alcohol vapors [Jensenius, H., J. Thaysen, A. A. Rasmussen, L. H. Veje, O. Hansen, and A. Boisen. A microcantilever-based vapor sensor-application and response model. Appl. Phys. Lett., 76, 2615–2617 (2000).] These cantilevers sensors were shown to have a detection limit below 10 ppm for alcohol vapor measurements. In similar work, volatile organic compounds were detected by monitoring the change in resonance frequency via a standard AFM set-up of polymer-coated microfabricated cantilevers. [Maute, M., S. Raible, F. E. Prins, D. P. Kem, H. Ulmer, U. Weimar, and W. Gopel. Detection of volatile organic compounds (VOCs) with polymer-coated cantilevers. Sensors and Actuators B, 58, 505–511 (1999).] In addition, commercial AFM microcantilevers have been coated with a polymer out of solution and antibodies for detection of ethanol and antigens, respectively, in an aqueous environment. [Tamayo, J., A. D. L. Humphris, A. M. Malloy, and M. J. Miles. Chemical sensors and biosensors in liquid environment based on microcantilevers with amplified quality factor. Ultramicroscopy, 86, 167–173 (2001).] The detection of analytes was made by simultaneously monitoring the deflection and the change in resonance frequency. In work by Betts et al., silicon microcantilevers were coated with thin films of polymeric chromatographic stationary phases via spin coating and then used for analyte vapor detection. [Betts, T. A., C. A. Tipple, M. J. Sepaniak, and P. G. Datskos. Selectivity of chemical sensors based on micro-cantilevers coated with thin polymer films. Anlytica Chimica Acta, 422, 89–99 (2000).]

In other work, researchers have fabricated piezoresistive polymer-coated cantilevers to be used as a component of multifaceted microsensors. [Lange, D., A. Koll, O. Brand, and H. Baltes. CMOS chemical microsensors based on resonant cantilever beams. Proc. SPIE, 3328, 233–243 (1998); Brand, O., M. Hornung, D. Lange, and H. Baltes. CMOS resonant microsensors. Proc. SPIE, 3514, 238–250 (1998).] Integration of these transducers with on-chip microelectronics enables for formation of a single-chip microsystem. For instance, merging a mass-sensitive polymer-coated piezoresistive microcantilever that detects a resonance frequency shift with capacitive and calorimetric transducers has facilitated the fabrication of a MEMS smart-chip chemical microsensor capable of detecting organic solvents. [Hagleitner, C., A. Hierlemann, D. Lange, A. Kummer, N. Kerness, O. Brand, and H. Baltes. Smart single-chip gas sensor microsystem. Nature, 414, 293–286 (2001); Hierlemann, A., A. Koll, D. Lange, C. Hagleitner, N. Kerness, O. Brand, and H. Baltes. CMOS-based chemical microsensors: components of a micronose system. Proc. SPIE, 3857, 158–169 (1999).]

Other groups have simply adsorbed a receptor molecule onto the surface of a microcantilever to create a microsensor. For instance, Illic et al. have demonstrated the ability to detect down to a single cell of *E. coli* (detecting a change in mass on the order of a fg) using a resonant frequency-based mass sensor based on a silicon nitride microcantilever with an immobilized antibody layer. This antibody layer was simply applied via adsorption on the surface of the microcantilever. [Ilic B., D. Czaplewski, M. Zalalutdinov, H. G. Craighead, P. Neuzil, C. Campagnolo, and C. Batt. Single cell detection with micromechanical oscillators. J. Vac. Sci. Technol. B., 19, 2825–2828 (2001); Ilic B., D. Czaplewski, H. G. Craighead, P. Neuzil, C. Campagnolo, and C. Batt. Mechanical resonant immunospecific biological detector. Applied Physics Letters, 77, 450–452 (2000).]

Microcantilevers have not just been utilized for detection of absorption or adsorption of an analyte on a coated or modified surface. For the development of an ultrasensitive infrared (IR) radiation microsensor, an array of ten bimaterial piezoresistive cantilevers was constructed to create a microcantilever calorimeter. [Abedinov, N., P. Grabiec, T. Gotszalk, T. Ivanov, J. Voight, and I. W. Rangelow. Micromachined piezoresistive cantilever array with integrated resistive microheater for calorimetry and mass detection. J. Vac. Sci. Technol. A, 19, 2884–2888 (2001).] The differential thermal expansion of the bimaterials resulted in a detectable bending of the cantilever. In similar work, Hu et al. used a bimaterial microcantilever (palladium/silicon) to investigate stresses as a result of the adsorption of mercury and the absorption of hydrogen. In other work. [Hu, Z., T. Thundat, and R. J. Warmack. Investigation of adsorption and absorption-induced stresses using microcantilevers. J. Appl. Phys., 90, 427–431 (2001).] Also, Datskos et al. detected bending due to adsorption-induced and photoinduced stresses on bimaterial microcantilevers for application in microsensors for chemical detection. [Datskos, P. G., M. J. Sepaniak, C. A. Tipple, and N. Lavrik. Photomechanical chemical microsensors. Sensors and Actuators B, 76, 393–402 (2001); Datskos, P. G., S. Rajic, M. J. Sepaniak, N. Lavrik, C. A. Tipple, L. R. Senesac, and I. Datskou. Chemical detection based on adsorption-induced and photoinduced stresses in microelectromechanical systems devices. J. Vac. Sci. Technol. B, 19, 1173–1179 (2001).]

Hydrogels

Hydrogels are mainly hydrophilic polymer networks that swell to a high degree due to an extremely high affinity for water, yet are insoluble because of the incorporation of chemical or physical crosslinks. Of note, hydrogels can absorb up to thousands of times their dry weight in water. Due to this high water content and the corresponding rubbery nature, hydrogels are similar to a variety of natural living tissues. This has led to widespread application of hydrogels as biomaterials, such as in contact lenses, sutures, dental materials, and controlled drug delivery devices. [Peppas, N. A. Hydrogels in Medicine and Pharmacy, CRC Press, Boca Raton, Fla., 1986; Hoffman, A. S. Hydrogels for biomedical applications. Adv. Drug Deliv. Revs., 54, 3–12 (2002).]

By tailoring the functional groups along the polymer chains, hydrogels can be made sensitive to the conditions of the surrounding environment, such as temperature, pH, electric field, or ionic strength. [Peppas, N. A. Physiologically responsive gels. J. Bioact. Compat. Polym., 6, 241–246 (1991).] Because of these favorable properties, extensive research has been focused on developing devices based on these hydrogels.

Environmentally Sensitive Hydrogels

Recent reviews have highlighted the extensive research focused on developing new and applying current environmentally sensitive hydrogels, specifically those sensitive to temperature, pH, and specific analytes. [Qiu, Y and K. Park.

Environment-sensitive hydrogels for drug delivery. Adv. Drug Deliv. Revs., 53, 321–339 (2001); Byrne, M. E., K. Park, and N. A. Peppas. Molecular imprinting within hydrogels. Adv. Drug Deliv. Revs., 54, 149–161 (2002); Jeong, B., S. W. Kim, and Y. H. Bae. Thermosensitive sol-gel reversible hydrogels. Adv. Drug Deliv. Revs., 54, 37–51 (2002); Miyata, T., T. Uragami, and K. Nakamae. Biomolecule-sensitive hydrogels. Adv. Drug Deliv. Revs., 54, 79–98 (2002)]. Temperature sensitive hydrogels are classified as either positive or negative temperature-sensitive systems, depending on whether they are contracted below or above a critical temperature, respectively. The majority of the research on thermosensitive hydrogels has focused on poly (N-isopropylacrylamide) (PNIAAm), which is a negative temperature-sensitive hydrogel exhibiting a phase transition around 33° C. PNIAAm and other thermosensitive hydrogels have been studied for variety of applications, including in drug delivery and tissue engineering. [Jeong, B., S. W. Kim, and Y. H. Bae. Thermosensitive sol-gel reversible hydrogels. Adv. Drug Deliv. Revs., 54, 37–51 (2002); Peppas, N. A., P. Bures, W. Leobandung, and H. Ichikawa. Hydrogels in pharmaceutical formulations. Eur. J. Pharm. Biopharm., 50, 27–46 (2000).]

The environmentally sensitive hydrogels that have received the most attention are those that demonstrate a reversible pH-dependent swelling behavior. These pH-sensitive hydrogels are usually based on ionic networks. Anionic networks contain acidic pendant groups, such as carboxylic acid, with a characteristic $pK_a$, while cationic networks contain basic pendant groups, such as amine groups, with a characteristic $pK_b$. In the case of anionic networks, ionization of these acid groups will occur once the pH of the environment is above the acid group's characteristic $pK_a$. With deprotonation of the acid groups, the network will have fixed charges on its chains resulting in an electrostatic repulsion between the chains and, in addition, an increased hydrophilicity of the network. Because of these alterations in the network, water is absorbed into the polymer to a greater degree causing swelling. This actuation process is shown in FIG. 2.

At the forefront of the field, researchers have created hydrogels that are sensitive to specific analytes. One method is to immobilize into pH-sensitive hydrogel networks enzymes that act on a specific analyte. In one study, activated glucose oxidase was included in pH-sensitive cationic hydrogels. [Podual, K., F. J. Doyle III, and N. A. Peppas. Glucose-sensitivity of glucose oxidase-containing cationic copolymer hydrogels having poly(ethylene glycol) grafts. J. Control Rel., 67, 9–17 (2000).] The glucose oxidase converts glucose into gluconic acid lowering the pH of the local environment, which then causes the hydrogel network to swell in the case of a cationic gel. This system was proposed for a responsive drug delivery system that would swell and release insulin in response to an increase in glucose concentration.

Another approach to impart analyte specificity, which is based on competitive binding, is to load a hydrogel containing the analyte in pendant groups with a corresponding entity that selectively binds the analyte. The entity will bind the pendent analytes and form cross-links in the network, which will then be broken with the competitive binding that takes place in the presence of the analyte. Kim et al. immobilized concanavalin A (Con A), a lectin (carbohydrate-binding proteins), in a hydrogel that contained glucose in its network. [Lee A. J. and K. Park. Synthesis and characterization of sol-gel phase-reversible hydrogels sensitive to glucose. J. Mol. Recognit., 9, 549–557 (1996).] The Con A non-covalently binds to the glucose pendent groups to form cross-links, and with increasing concentration of glucose in the environment, the cross-links are reversibly broken allowing the network to swell.

Hydrogels on the Micro-scale

Over the years, hydrogels have been the focus of widespread interest for the macro-scale applications mentioned above. With the increase of research interested in miniaturization in recent years, a new dimension has been added to the applicability of hydrogels.

A number of research groups have micropatterned hydrogels for application in biomaterials and biosensors. Ito described patterning hydrogels and other polymers for application in regulating cell functions. [Ito, Y. Surface micropatterning to regulate cell functions. Biomaterials, 20, 2333–2342 (1999).] In additional work, Ito and collaborators have patterned pH-sensitive and thermo-sensitive hydrogels and proposed these microstructures for use in various microdevices. [Ito, Y. Photolithographic synthesis of intelligent microgels. Journal of Intelligent Material Systems and Structures, 10, 541–547 (1999); Chen, G., Y. Imanishi, and Y. Ito. Photolithographic synthesis of hydrogels. Macromolecules, 31, 4379–4381 (1998); Chen, G., Y. Ito, and Y. Imanishi. Micropattern immobilization of a pH-sensitive polymer. Macromolecules, 30, 7001–7003 (1997).] In numerous studies done by Matsuda and coworkers, hydrogels have been micropatterned to create surface regions with different physicochemical properties for direction of cell adhesion and behavior. [Nakayama, Y., J. M. Anderson, and T. Matsuda. Laboratory-scale mass production of a multi-micropatterned grafted surface with different polymer regions. J. Biomed. Mater. Res. (Appl. Biomater.), 53, 584–591 (2000); DeFife, K. M., E. Colton, Y. Nakayama, T. Matsuda, and J. M. Anderson. Spatial regulation and surface chemistry control of monocyte/macrophage adhesion and foreign body giant cell formation by photochemically micropatterned surfaces. J. Biomed. Mater. Res., 45, 148–154 (1999); Higashi, J., Y. Nakayama, R. E. Marchant, and T. Matsuda. High-spatioresolved microarchitectural surface prepared by photograft copolymerization using dithiocarbamate: surface preparation and cellular responses. Langmuir, 15, 2080–2088 (1999); Nakayama, Y., K. Nakamata, Y. Hirano, K. Goto, and T. Matsuda. Surface hydrogelation of thiolated water-soluble copolymers on gold. Langmuir, 14, 3909–3915 (1998); Nakayama, Y. and T. Matsuda. Surface macromolecular architectural designs using photo-graft copolymerization based on photochemistry of benzyl n,n-diethyldithio-carbamate. Macromolecules, 29, 8622–8630 (1996).] This work was based on a surface polymerization technique induced by an iniferter (acts as an initiator, a transfer agent, and a terminator). In this work, hydrogels have been micropatterned to create surface regions with different physico-chemical properties for direction of cell adhesion and behavior. In addition, Beebe and coworkers have micropatterned hydrogels within a microchannel to be used as a valve that can sense a pH change and actuate for use in microdevice applications. [Beebe, D. J., J. S. Moore, J. M. Bauer, Q. Yu, R. H. Liu, C. Devadoss, and B. Jo. Functional hydrogel structures for autonomous flow control inside microfluidic channels. Nature, 404, 588–590 (2000); Beebe, D. J., J. S. Moore, Q. Yu, R. H. Liu, M. L. Kraft, B. Jo, and C. Devadoss. Microfluidic tectonics: a comprehensive construction platform for microfluidic systems. Proc. Natl. Acad. Sci. U.S.A., 97, 13488–13493 (2000).] Ward et al.

patterned poly(ethylene glycol)-containing hydrogels onto polymer substrates that had incorporated iniferters in their networks to provide bonding and were able to create novel surfaces for possible application in biosensors and in biomaterials for selective adhesion of cells and proteins. [Ward, J. H., R. Bashir, and N. A. Peppas. Micropatterning of biomedical polymer surfaces by novel UV polymerization techniques. J. Biomed. Mater. Res., 56, 351–360 (2001).] These examples utilize two advantageous properties of hydrogels, high biocompatibility and sensing/actuating, respectively.

In additional work, several groups have focused on developing microdevices utilizing environmentally sensitive hydrogels as microactuators. Beebe et al. [Beebe, D. J., J. S. Moore, J. M. Bauer, Q. Yu, R. H. Liu, C. Devadoss, and B. Jo. Functional hydrogel structures for autonomous flow control inside microfluidic channels. Nature, 404, 588–590 (2000); Beebe, D. J., J. S. Moore, Q. Yu, R. H. Liu, M. L. Kraft, B. Jo, and C. Devadoss. Microfluidic tectonics: a comprehensive construction platform for microfluidic systems. Proc. Natl. Acad. Sci. U.S.A., 97, 13488–13493 (2000)] and Zhao et al. [Zhao, B. and J. S. Moore. Fast pH- and ionic strength-responsive hydrogels in microchannels. Langmuir, 17, 4758–4763 (2001)] have micropatterned pH-sensitive hydrogels inside microfluidic channels to create flow controls that could sense the environmental conditions and then actuate in response. In similar work, pH-sensitive hydrogels were patterned to form a biomimetic valve capable of directional flow control. [Yu, Q, J. M. Bauer, J. S. Moore, and D. J. Beebe. Responsive biomimetic hydrogel valve for microfluidics. Appl. Phys. Lett., 78, 2589–2591 (2001).] Similarly, Madou and coworkers have utilized a blend of redox polymer and hydrogel to create an "artificial muscle" that can act as an electro-actuated microvalves for possible application in controlled drug delivery. [Low, L., S. Seetharaman, K. He, and M. J. Madou. Microactuators toward microvalves for responsive controlled drug delivery. Sensors and Actuators B, 67, 149–160 (2000).]

Furthermore, environmentally sensitive hydrogels have been applied as sensing elements in a variety of microsensor applications. To create biosensors for monitoring various analyte levels, several research groups have patterned hydrogels containing immobilized oxidoreductase enzymes, such as glucose oxidase, lactate oxidase, and alcohol oxidase, onto electrodes using photolithography [74–76]. In similar work, Sheppard et al. developed a miniature conductimetric pH sensor based on the measurement of the conductivity of a pH-sensitive hydrogel that was photolithographically patterned onto planar interdigitated electrode arrays [77, 78]. In another study, pH-sensitive hydrogels were photolithographically patterned for possible application in a fluorescence sensor array [79]. Moreover, Hu et al. patterned environmentally sensitive hydrogels for possible application in display and sensor technologies [80].

Therefore, the development of microfabrication techniques has opened the door for the creation of a wide array of new devices. In particular, MEMS sensors and specifically those based on ultrasensitive microcantilevers have been applied in a wide variety of applications. In parallel, hydrogels and their well-known attractive macroscale properties have been extended for application on the microscale. At this dimensionality, researchers have realized novel applications for environmentally sensitive hydrogels, including in sensor applications.

SUMMARY OF THE INVENTION

The present invention is directed in part to a microsensor element in the form of a microscale cantilever suitably functionalized for implementing an electronic microbiological assay device. Pursuant to the present invention the microscale cantilevers are functionalized with hydrogels.

The present invention recognizes the ability of hydrogels to sense an environmental condition and actuate in response made them a sensible option in a microsensor device. Additionally, the invention capitalizes on the ultrasensitivity of microcantilevers as a transducer element. The invention combines the ultrasensitivity of the microcantilever with the sensing and actuating ability of an environmentally sensitive hydrogel to create a MEMS sensor.

One environmental condition that may be monitored via a hydrogel is acidity. An increase in acidity is indicative of living cells. A monitoring apparatus useful in detecting viability of biological cells comprises, in accordance with the present invention a substrate defining a microscopic chamber, at least one microcantilever connected to the substrate and extending into the chamber, a detector operatively connected to the microcantilever for sensing a state of deformation thereof, and a layer of an environmentally sensitive hydrogel polymer provided on at least one surface of the microcantilever, the hydrogel polymer having a configuration changing in accordance with presence and absence of an environmental parameter.

The environmental parameter may be a chemical species. Where the chemical species is the hydrogen ion, the state of deflection of the microcantilever is indicative of the pH of the liquid. In this case, hydrogel polymer is a cross-linked network of hydrophilic monomers preferably taken from the group consisting of unsaturated organic acid monomers, acrylic substituted alcohols, and acrylamides. More particularly, the monomers are taken from the group consisting of methacrylic acids, acrylic acids, glycerolacrylate, glycerolmethacrylate, 2-hydroxyethylmethacrylate, 2-hydroxyethylacrylate, 2-(dimethylaminoethyl methacrylate, N-vinyl pyrrolidone, methacrylamide, and N,N-dimethylacrylamide poly(methacrylic acid) containing amounts of poly(ethylene glycol) n dimethacrylate, where n is the average molecular weight of the PEG chain. In the last case, the average molecular weight of the PEG chain is preferably between about 50 and about 500 and more preferably about 200.

Where the chemical species is glucose, the hydrogel polymer may take the form of a boronate-containing polymer complex that swells due to diffusion of ion species upon chemical responsiveness when in contact with glucose.

The environmental parameter may be temperature. In that case the hydrogel polymer may be poly(N-isopropylacrylamide) (PNIAAm) or may be alternatively obtained by polymerizing in an aqueous solution, N-alkyl acrylamide derivatives with acrylic acid, alkali metal salts of acrylic acid, or mixtures thereof, and diacetone acrylamide.

A method for the detection of cell viability utilizes, in accordance with the present invention, a solid state microbiological testing device including a microcantilever coated on at least one side with a hydrogel polymer sensitive to an environmental parameter modifiable by cellular metabolism, the microcantilever projecting into a chamber. The method includes feeding a liquid to the chamber, the liquid containing at least one biological cell, and automatically monitoring a state of deflection of the microcantilever to determine a change in a state of the microbiological parameter owing to metabolic activity of the biological cell.

Where the environmental parameter is the hydrogen ion, a measurement of pH determines whether the biological cell or cells have generated acids (e.g., lactic acid, acetic acid), as a result of natural metabolic activity.

Rather than monitoring a product of cellular metabolism, a hydrogel-coated microcantilever may be used to monitor a chemical species which is a raw material of cellular metabolism. For example, where a monitoring of glucose levels in the test liquid reveals a fall in glucose concentration, that change may be indicative of ongoing cellular metabolism. To detect glucose concentration, the hydrogel polymer may take the form of a boronate-containing polymer complex that swells due to diffusion of ion species upon chemical responsiveness when in contact with glucose.

The environmental parameter may be temperature. In that case, the hydrogel polymer may take the form of poly(N-isopropylacrylamide) (PNIAAm) or may be obtained by polymerizing in an aqueous solution, N-alkyl acrylamide derivatives with acrylic acid, alkali metal salts of acrylic acid, or mixtures thereof, and diacetone acrylamide. The monitoring of temperature is indicative of cell viability insofar as cellular metabolism is an exothermic process. The use of temperature as the environmental indicator of active cellular processes requires that the sensor apparatus be adequately insulated thermally. Generally, where the volume of the detection chamber is sufficiently small relative to the chip as a whole (2%–25%), the silicon substrate will have sufficient thermal inertia so that a temperature rise owing to cellular metabolism can be easily detected.

The automatic monitoring of the state of deflection of the microcantilever may be implemented by any known method including, but not limited to, resistively sensing the state of deflection, optically sensing the state of deflection, and monitoring a resonance circuit including an element on the microcantilever. Other methods available to those skilled in the art may entail magnetic measurements.

A method for manufacturing a microsensor comprises, in accordance with the present invention, providing a silicon substrate having a structural element, bonding an organosilane coupling agent to the structural element, thereafter applying a monomer mixture to the structural element over the coupling agent to form a monomer layer, subsequently contacting the monomer layer with a mask, using a commercial mask aligner to align a pattern in the mask with the structural element to expose the structural element and the monomer thereon, treating the exposed monomer on the structural element with ultraviolet radiation, removing the mask from unexposed monomer on the substrate, and washing away the unexposed monomer from the substrate.

This method is particularly effective where the structural element is a microcantilever.

The manufacturing method may additionally comprise using an initiator in an increased amount, while the treating of the exposed monomer with ultraviolet radiation may extend over a period of time which is longer than in conventional processing methods.

The organosilane coupling agent preferably has the structure $RSiX_3$, where X is a hydrolyzable group that can react and covalently bond with hydroxylated substrates. The organosilane coupling agent is formable as a self-assembled monolayer on a silicon dioxide surface of the structural element.

The applying of the monomer mixture may be achieved by spray-coating or spin-coating the monomer mixture.

A microscale microbiological assay device in accordance with the present invention provides an ultrasensitive microsensing capability. The sensing function is integrated into microdevices to enable analysis of micro-scale sample volumes. These microsystems that can fit on a single chip facilitate the fabrication of portable, hand-held, and even implantable devices as improved analysis systems. For example, implantable devices, containing a microsensor that monitors a physiological condition, can be used to initiate a treatment when a predetermined signal is measured.

A microsensor pursuant to the present invention is based on a microcantilever patterned with an environmentally sensitive hydrogel. Microcantilevers have been used as ultrasensitive sensors while hydrogels have been shown to reversibly sense and actuate under varying conditions of their environment, but prior to the present invention their favorable properties have not been combined. The present invention provides a technique for precisely patterning environmentally sensitive hydrogels onto silicon substrates. The present invention also provides a method for promoting adhesion between the dissimilar silicon and polymer. In a related development, the present invention provides a technique for precisely patterning environmentally sensitive hydrogels onto microcantilevers.

One environmentally sensitive polymer utilizable in the present invention is a crosslinked poly(methacrylic acid) containing large amounts of poly(ethylene glycol) n dimethacrylate, where n is the average molecular weight of the PEG chain (n=200). This hydrogel exhibits a swelling dependence on the environmental pH. Other, ionic, polymers utilizable in functionalizing a microscale cantilever in accordance with the present invention include poly(acrylic acid), polyacrylamide (PAAm), poly(diethylaminoethyl methacrylate), and poly(dimethylaminoethyl methacrylate).

The prior art approaches described above for imparting analyte specificity, which are based on competitive binding, have been proven effective in producing analyte sensitive hydrogels. However, those prior art approaches rely on proteins, which inherently leads to limitations in the system. An alternative to these techniques is to use synthetic biomimetic networks to create hydrogels that will bind and respond to specific analytes. Several methods are possible which utilize molecular imprinting processes to design analyte responsive hydrogels that can respond, in theory, to any desired analyte. [See Byrne, M. E., K. Park, and N. A. Peppas. Molecular imprinting within hydrogels. Adv. Drug Deliv. Revs., 54, 149–161 (2002).] These methods enable for analyte responsive hydrogels to be created for a variety of applications.

For the use of polymers in MEMS and other devices containing microelectronics, it is beneficial to use silicon substrates to enable simple integration with microelectronics. In addition, precise spatial control over polymer microstructures is key for their application into microdevices. Photolithography utilizing a mask aligner allows for this critical spatial control of the polymer microstructures. The present invention contemplates the use of microfabrication techniques based on UV free-radical polymerizations using a commercial mask aligner to facilitate the creation of polymer micropatterns on silicon for incorporation into microdevices. These methods are the foundation for the integration of environmentally sensitive hydrogels into silicon MEMS sensors.

The present invention in part provides a process for micropatterning thin environmentally sensitive polymer onto silicon substrates with precise positioning. Thin films are patterned through utilizing a mask aligner in air via free radical polymerization. Adhesion between the thin polymer film and the silicon substrate is attained. Specifically, these techniques are applicable for patterning onto microcantilevers with thicknesses of approximately 1 $\mu$m. In such cases, the environmentally sensitive hydrogel film needs to be on the order of 1 µm in thickness. This process allows for the integration of environmentally sensitive hydrogels into silicon microdevices.

DEFINITIONS

Figure 1:
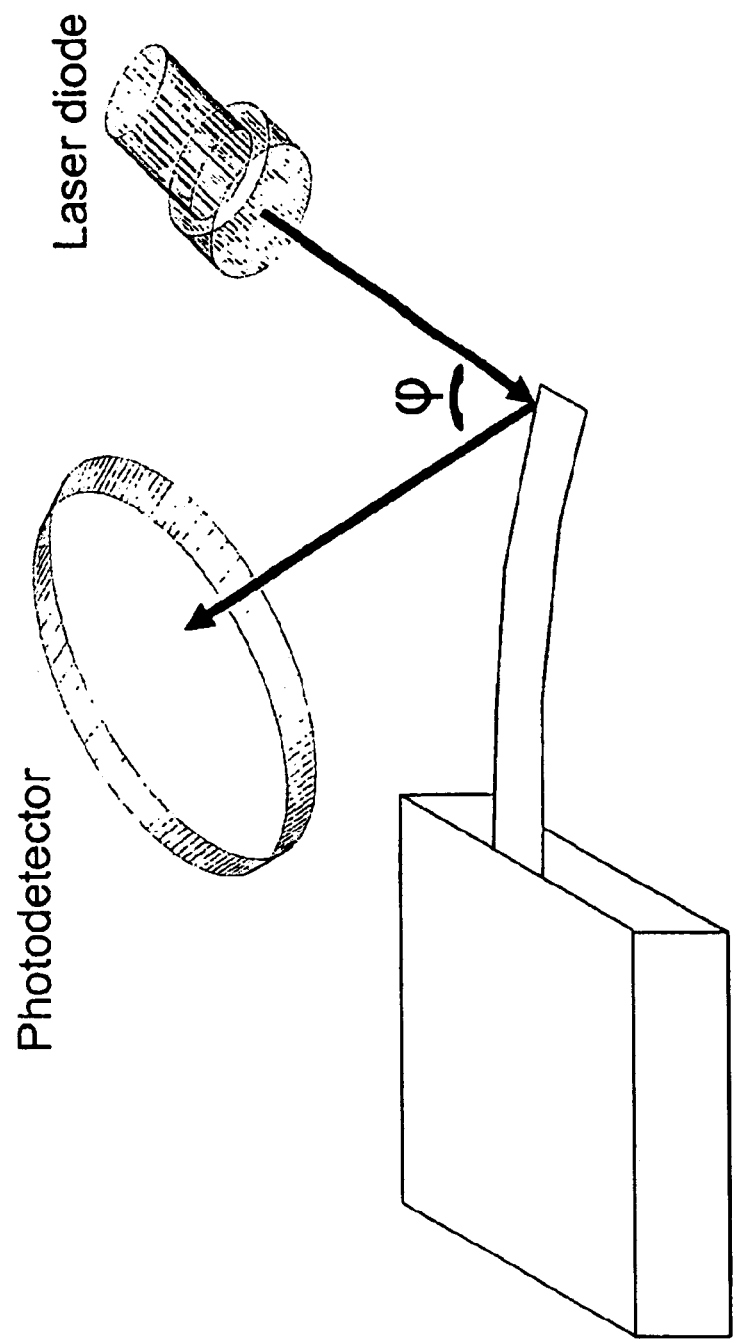
FIG. 1 is a schematic diagram showing a technique using a low power laser diode 20 for monitoring deflection of a microscale cantilever 24.
Figure 2:
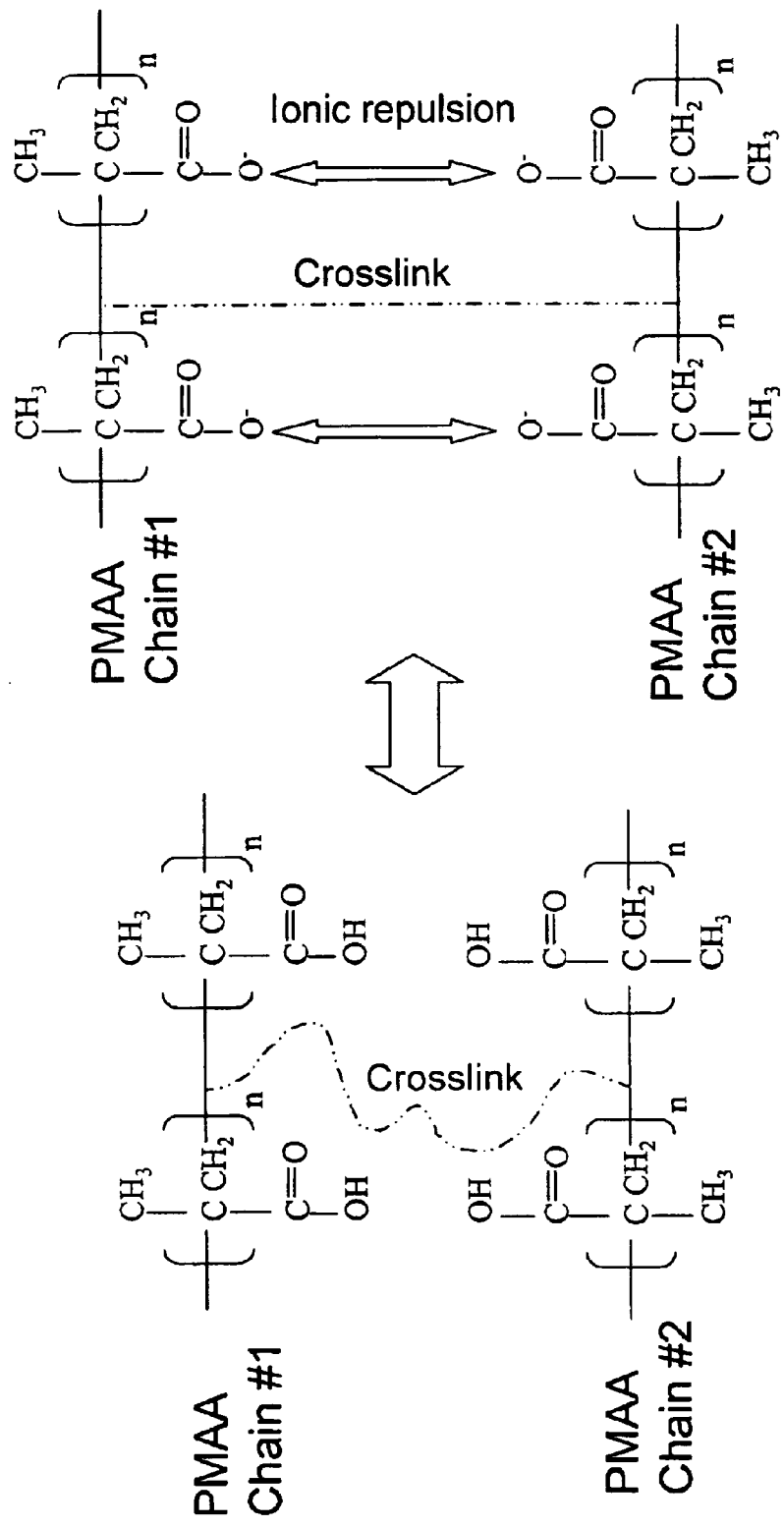
FIG. 2 is a diagram of chemical structure illustrating structural changes associated with swelling in a hydrogel.

The word "microscale" and the associated prefix "micro-" are used herein to denote dimensions of a microscopic size. More particularly, the dimensions contemplated extend from a few hundredths of a micron to several hundred microns.

The term "cantilever" or "microcantilever" is used herein to denote any structural element that is so anchored as to have at least one degree of freedom, enabling movement in at least one dimension. The movement is usually a bending, rotational and/or torsional motion. For purposes of the present disclosure, the movement occurs in response a conformation change of a hydrogel layer provided on at least one surface of the cantilever or microcantilever. A cantilever or microcantilever generally has one end fixed to a substrate and an opposite end which is free and unattached. For example, a cantilever or microcantilever may take the form of a planar finger-like projection extending from a base or substrate into a space such as a liquid-containing chamber. Generally, microcantilevers are made of a semiconductor material. However other materials may be used, provided that such materials are capable of being fabricated in the requisite size, for instance, by a mask aligner. Microcantilevers are of a microscopic size, with a thickness on the order of 1 μm (e.g., 800 nm), a width on the order of 10 μm (e.g. 30 μm), and a length on the order of 100 μm (e.g., 200 or 300 μm).

Terms such as "deformation detector" or "deflection sensor" are used herein to denote conventional electrical and/or optical circuit elements designed to detect changes in conformation or configuration of a structure such as a microcantilever. The "deformation detector" or "deflection sensor" may optionally measure the degree of the deformation or change in configuration. Deformation detectors or sensors may be resistive, optical or resonant. In the case of a resistive-type detector or sensor, piezoelectric circuit elements incorporated into the microcantilever are sensitive to changes in dimension. In the case of optical monitoring device, a laser beam is aimed at the subject microcantilever, a reflected beam being monitored by an optical sensor. Motion of the point of incidence of the reflected beam on the sensor is a measure of the movement of the microcantilever. Where resonance is used to monitor microcantilever deformation, a circuit element on the microcantilever is included in a resonant circuit. A deformation of the microcantilever changes the resonant frequency. All of these measurement techniques are well-known in the art and can be implemented without additional explanation.

The term "hydrogel" or "hydrogel polymer" is used herein to denote hydrophilic polymer networks that swell to a high degree due to an extremely high affinity for water, yet are insoluble because of the incorporation of chemical or physical crosslinks. Hydrogels can absorb up to thousands of times their dry weight in water.

The term "environmentally sensitive" as used herein refers to the ability or propensity of hydrogels to change their conformation or configuration in response to changes in environmental conditions. By definition, all hydrogels are sensitive to moisture. Under dry conditions, a hydrogel network occupies a relatively small volume. When wetted, the hydrogel absorbs water molecules and spreads out. Changes in other environmental conditions will affect only some hydrogels. Such environmental conditions include pH and temperature, as well as the presence or absence of specific analytes such as glucose in a solution.

A pH-sensitive hydrogel as described herein is a hydrogel made in part from hydrophilic monomers which incorporate separable proton species into the polymer mass. These protons establish, with an aqueous solution, an equilibrium depending on the acidity of the solution. Suitable hydrophilic monomers include unsaturated organic acid monomers, more particularly carboxylic acid monomers such as methacrylic and acrylic acids. Other suitable monomers include glycerolacrylate and glycerolmethacrylate, and acrylic substituted alcohols such as 2-hydroxyethylmethacrylate and 2-hydroxyethylacrylate. A related utilizable polymer is formed from 2-(dimethylaminoethyl methacrylate (DMAEMA), which introduces an amine group onto the polymer backbone. Here, a lightly crosslinked polyHEMA-co-DMAEMA could be used since it swells at low pH when the amine group is protonated. Further suitable monomers include N-vinyl pyrrolidone and acrylamides such as methacrylamide and N,N-dimethylacrylamide, among numerous others which will be apparent to those skill in the art. In a particular embodiment of the present invention, the pH-sensitive hydrogel polymer provided on a microcantilever is a crosslinked poly(methacrylic acid) containing amounts of poly(ethylene glycol) n dimethacrylate, where n, the average molecular weight of the PEG chain, is preferably between about 50 and about 500 and more preferably about 200.

A temperature-sensitive or thermosensitive hydrogel as described herein is a hydrogel which volumetrically expands in response to a temperature change. Thus, the degree of expansion or contraction of the hydrogel is dependent on temperature. Temperature sensitive hydrogels are classified as either positive or negative temperature-sensitive systems, depending on whether they are contracted below or above a critical temperature, respectively. Examples of thermosensitive hydrogels include poly(N-isopropylacrylamide) (PNIAAm), which is a negative temperature-sensitive hydrogel exhibiting a phase transition around 33° C. More generally, a temperature sensitive water absorbing and discharging polymer composition having a predetermined selected temperature sensing point, which controls water absorbability, is obtained by polymerizing in an aqueous solution, N-alkyl acrylamide derivatives with acrylic acid, alkali metal salts of acrylic acid, or mixtures thereof, and diacetone acrylamide. As disclosed in U.S. Pat. No. 5,672,656, the disclosure of which is incorporated by reference, the temperature sensitive water absorbing and water discharging polymer composition may be modified to control the temperature sensing point and has a high water discharging and absorbing property above and below the temperature sensing point.

An analyte-sensitive hydrogel as described herein contains a chemical component that is in equilibrium with the same chemical component (analyte) in solution or that reacts with another chemical species (analyte) in solution. Where a hydrogel layer is in contact with a liquid, presence of a target analyte in the liquid or, more generally, a change in the concentration of the target analyte in the liquid, induces a conformation change of the hydrogel layer. Generally, the conformational change is an expansion or contraction which in turn causes a movement of a microcantilever on which the hydrogel is disposed. In one embodiment, a glucose-sensitive hydrogel includes activated glucose oxidase in a pH-sensitive cationic hydrogels. [See Podual, K., F. J. Doyle III, and N. A. Peppas. Glucose-sensitivity of glucose oxidase-containing cationic copolymer hydrogels having poly(ethylene glycol) grafts. J. Control Rel., 67, 9–17 (2000).] The glucose oxidase converts glucose into gluconic acid lowering the pH of the local environment, which then causes the hydrogel network to swell in the case of a cationic gel. In another example where glucose is the target analyte, a hydrogel has boronate-containing polymer complexes that swell due to diffusion of ion species upon chemical responsiveness when in contact with glucose.

DETAILED DESCRIPTION OF THE PREFERRED EMBODIMENTS

Detection of cell viability is accomplished using a solid-state microbiological testing device including a structural element such as a microcantilever coated on at least one side with a hydrogel polymer. The polymer is sensitive to an environmental parameter which is typically affected by cellular metabolism. The environmental parameter might be acidity or pH level, which is subject to chemical by-products of metabolic processes, such as lactic acid and acetic acid. Alternatively, the environmental parameter may be an analyte such as glucose which is a raw material used up by cellular metabolic processes. Another environmental parameter affected by cellular processes is temperature.

The microcantilever is in contact with a chamber into which is fed a liquid containing one or more biological cells to be tested for viability. The viability of the cells is determined by automatically monitoring a state of deflection of the microcantilever. Where the cells are biologically active, they modify the state or concentration of the environmental parameter. That modification in turn changes the degree of expansion or contraction of the hydrogel polymer. The deformation of the hydrogel polymer then exerts a force on the microcantilever causing a deflection which is detectable by any known technique including resistive sensing, optical sensing, and resonance circuit monitoring.

Manufacturing of Microscale Cantilevers

Microscale cantilevers utilizable in MEMS devices are provided on one side with an environmentally sensitive hydrogel such as crosslinked poly(methacrylic acid) containing large amounts of poly(ethylene glycol) n dimethacrylate, poly(acrylic acid), polyacrylamide (PAAm), poly(diethylaminoethyl methacrylate), and poly(dimethylaminoethyl methacrylate). The hydrogels are patterned onto the silicon or silicon-nitride cantilevers using a commercial mask aligner.

Manufacturing: Free Radical Polymerization of Thin Films in Air

In free radical polymerizations, inhibitors can impede the polymerization reaction by reacting with the initiating and propagating radicals converting them into either nonradical species or radicals of low reactivity that will terminate propagation. When polymerizing in air, oxygen inhibits free radical polymerizations by reacting with radicals to form relatively unreactive peroxy radical [11]:

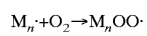

This peroxy radical will then react with itself or another propagating radical by coupling and disproportionation reactions leading to inactive products. To prevent this inhibition, free radical polymerizations are typically performed in an inert gas environment, such as nitrogen, argon, or in vacuum.

The precise micropatterning of hydrogel polymers is done with a commercial mask aligner, which does not easily facilitate polymerization in an inert gas environment. In addition, because the hydrogel is deposited in thin layers, oxygen can rapidly diffuse into the film, thereby enhancing the inhibition effect. For polymerization of micropatterns under these conditions, several experimental parameters are modified, including extending UV exposure lengths, increasing initiator amount, and providing a barrier to diffusion of oxygen into the monomer.

Manufacturing: Polymer/Silicon Adhesion

Due the dissimilar properties of silicon and polymer, a bridge is needed to provide for bonding of these two materials. For example, adhesion can be gained between silicon and polymer via the application of an organosilane coupling agent. The organosilane coupling agent typically has the structure $RSiX_3$, where X is a hydrolyzable group that can react and covalently bond with hydroxylated substrates, such as the silanol groups on silicon dioxide. (See Plueddemann E. P., Silane Coupling Agents, $2^{nd}$ Edition. Plnuem Press, New York, 1991.) This process results in the formation of self-assembled monolayers with the organofunctional group, R, presented on the surface, and this R group can be tailored to provide a desired surface modification. For adhesion to polymer, this organofunctional group is chosen to have a high reactivity with the polymer. The organosilane coupling agent utilized may contain a methacrylate organofunctional group that can react with the monomers and oligomers and be included in the polymer network resulting in covalent adhesion.

Manufacturing Process: Example

Figure 3:
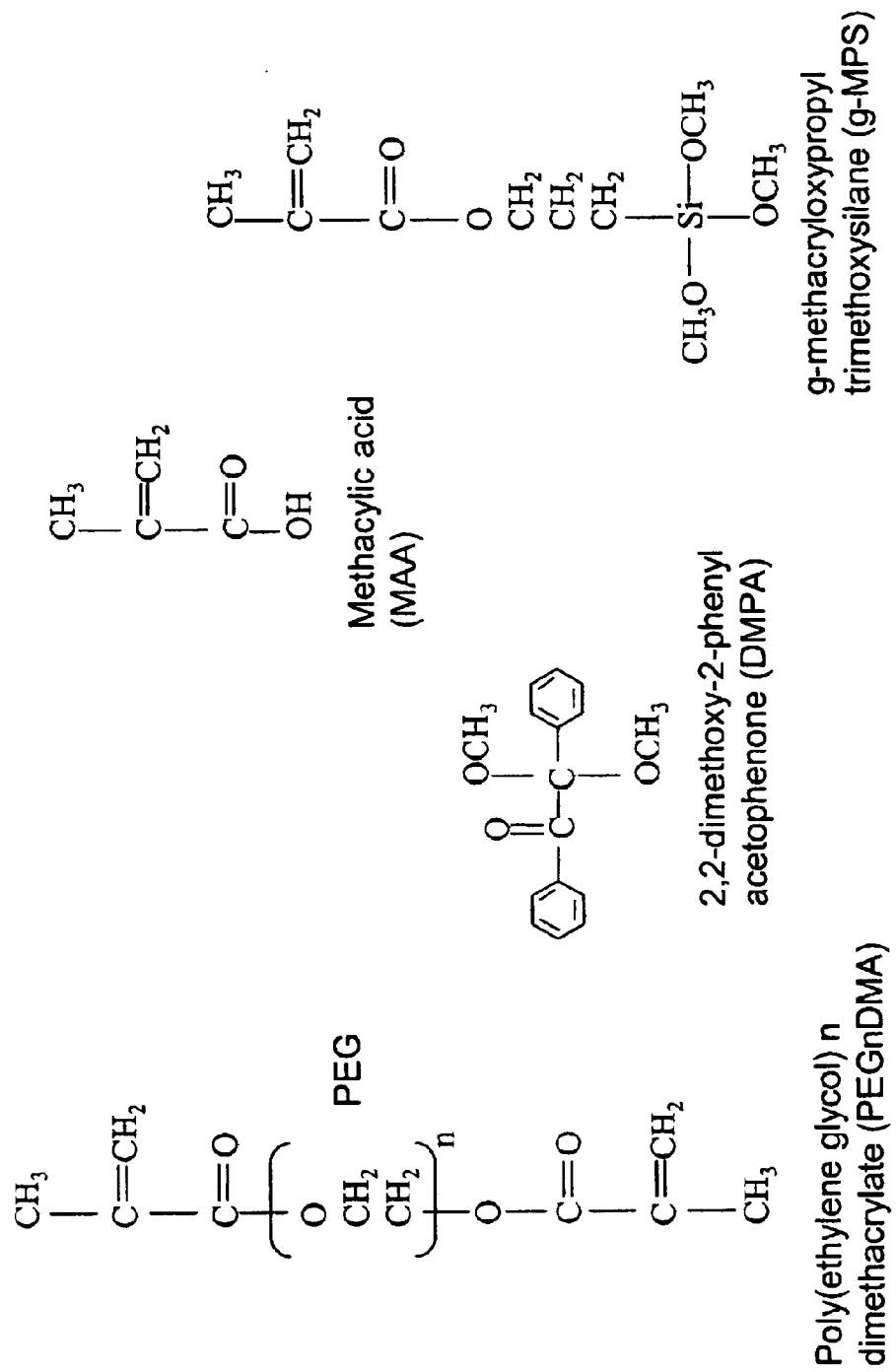
FIG. 3 is a diagram of monomers and other chemicals used in a manufacturing process in accordance with the present invention.

A crosslinked poly(methacrylic acid) (PMAA) network containing significant amounts of poly(ethylene glycol) dimethacrylate (PEGnDMA) was used. This hydrogel exhibits a swelling dependence on environmental pH. The monomers used were methacrylic acid (MAA) and poly(ethylene glycol) n dimethacrylate (PEGnDMA), where n is the average molecular weight of the PEG chain (n=200). The initiator used for the UV free radical polymerization was 2,2-dimethoxy-2-phenyl acetophenone (DMPA), and adhesion was gained between the silicon substrate and the polymer using an organosilane coupling agent, γ-methacryloxypropyl trimethoxysilane (γ-MPS). The MAA, DMPA, and γ-MPS were purchased from Aldrich (Milwaukee, Wis.). PEGnDMA, with n=200, was obtained from Polysciences, Inc. (Warrington, Pa.). The structures of these monomers and chemicals are shown in FIG. 3.

Silicon wafers were cleaved into pieces that were approximately 2 cm by 2 cm. These silicon pieces were then cleaned utilizing a standard industry Piranha wafer clean. The wafers were first soaked in deionized distilled water for 2 minutes to provide for a general rinse, followed by submersion in a Piranha solution ($H_2O_2:H_2SO_4$, 1:1) for 15 minutes. This cleaning removed any organic residues and dust, and in addition, it chemically grew a thin layer of silicon dioxide on the silicon surface. This thin silicon dioxide film was utilized later for the bonding of the polymer to the silicon with the organosilane coupling agent. Lastly, the pieces were again soaked in deionized distilled water to remove any residual chemicals from the cleaning process.

To achieve adhesion between the silicon surface and the polymer, an organosilane coupling agent was utilized. The silicon pieces were soaked in a 10 wt % solution of γ-MPS in acetone for more than 2 hours. Then, these were rinsed in acetone followed by ethanol, and then air-dried. As described above, the organosilane coupling agent formed a self-assembled monolayer on the silicon dioxide surface and presented methacrylate pendant groups that reacted and bonded with the polymer film. A schematic of this process is included as FIG. 4.

Figure 5:
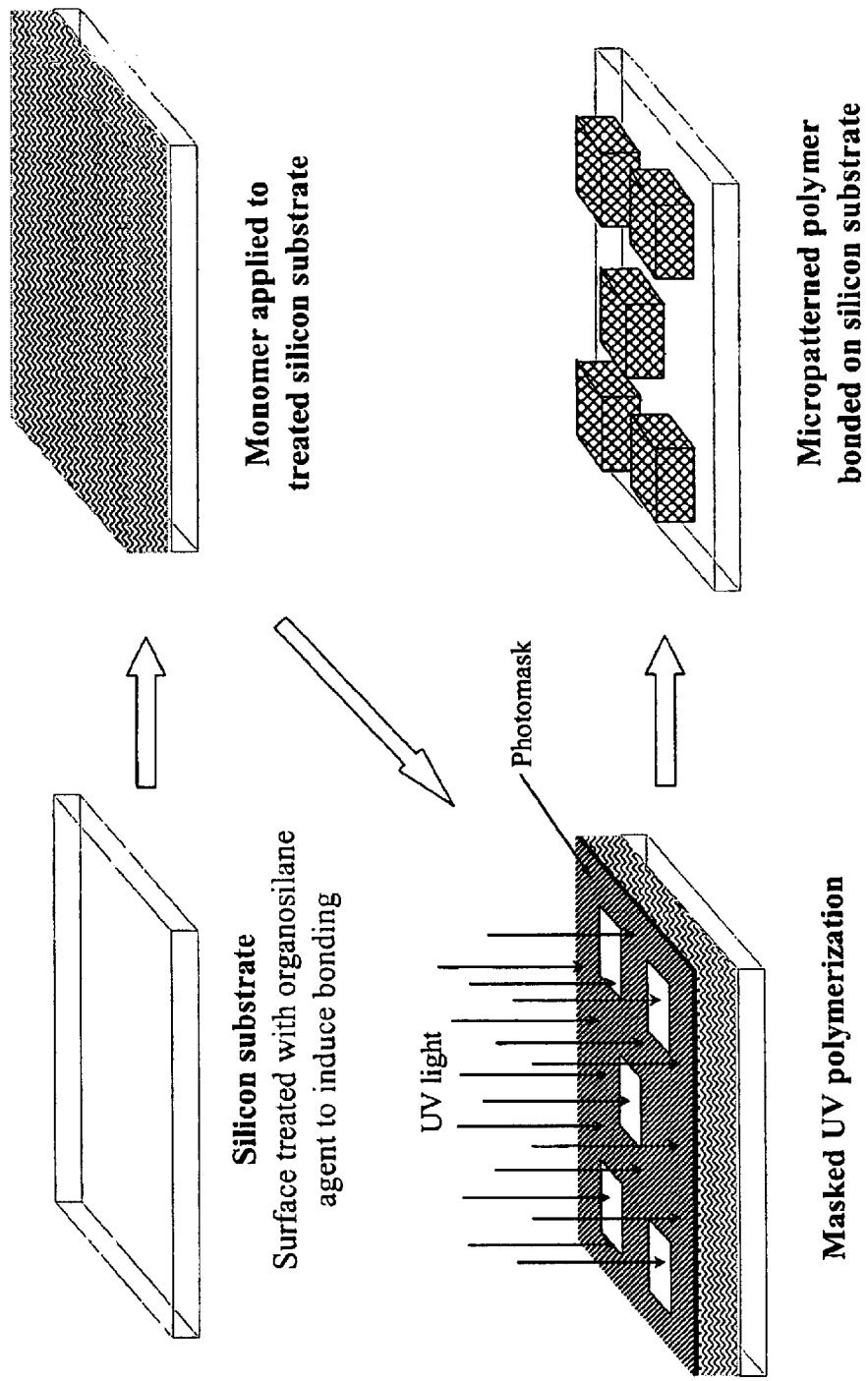
FIG. 5 is a diagram showing successive steps in a patterning of hydrogel polymer onto a silicon substrate in a manufacturing method in accordance with the present invention.

The monomer mixtures were prepared with a mole ratio of 80:20 MAA:PEGnDMA, where n=200, and containing between 1 and 10 wt % DMPA. The monomer mixture was either spray-coated or spin-coated (for 30 seconds) onto the silicon pieces. Next, polymer micropatterns were created by UV free-radical polymerization using a Karl Suss MJB3 UV400 mask aligner. The Karl Suss MJB3 UV400 mask aligner enabled for alignment accuracies of 0.1 microns. The photomask was fabricated at the Purdue ECE Solid State Lab. The mask is made on a photoplate purchased from Nanofilm. It is 4"×4"×0.6" low reflectance chrome on white crown substrate. After bringing the sample into contact with or in the proximity of the mask, the sample was exposed to UV light with intensity of 23.0 mW/cm$^2$ for exposure times of 1 to 20 minutes. The pieces were then removed and allowed to soak in deionized distilled water for greater than 24 hours to remove any unreacted monomer. FIG. 5 is a schematic of the procedure for micropatterning onto a silicon substrate.

The final samples of the patterned polymer were examined several ways. To examine the micropatterned features, the optical microscope system utilized was a Nikon Industrial Microscope Eclipse L150 equipped with a Insight Digital Camera with KAI-2000 Mosaic CCD, allowing for images to be taken with 50×, 100×, 200×, 500×, and 1000× magnification. A profilometer (alpha-step 200, Tencor Instruments, San Jose, Calif.) was also used to determine the height and profile of the pattern.

Bulk Equilibrium Swelling Studies

Bulk equilibrium swelling studies were conducted to gain an understanding of this polymer's response to varying pH and its dependence on initiator amount.

Figure 6:
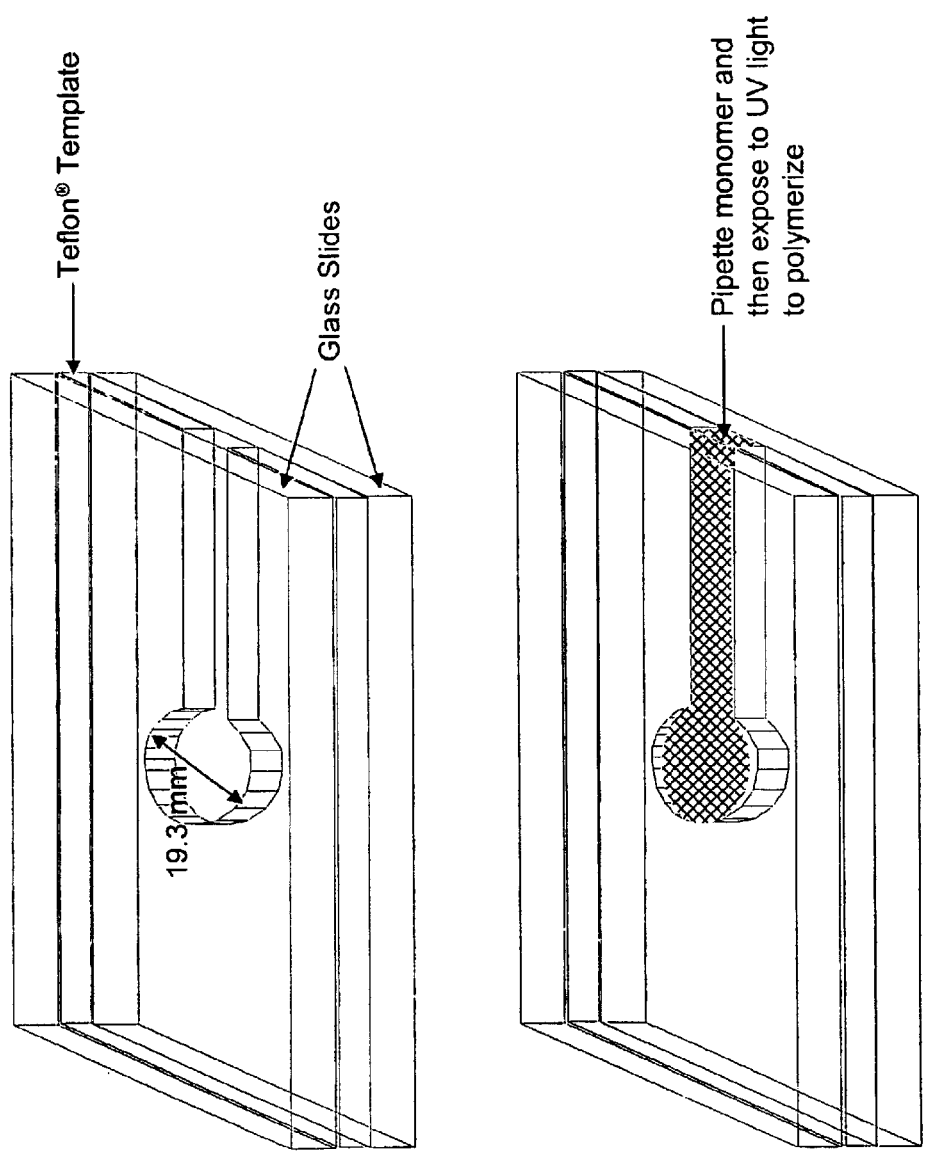
FIG. 6 is a schematic isometric view of a polytetrafluorethylene template sandwiched between a pair of glass slides, showing a process for preparing bulk polymer discs for equilibrium swelling studies.
Figure 7:
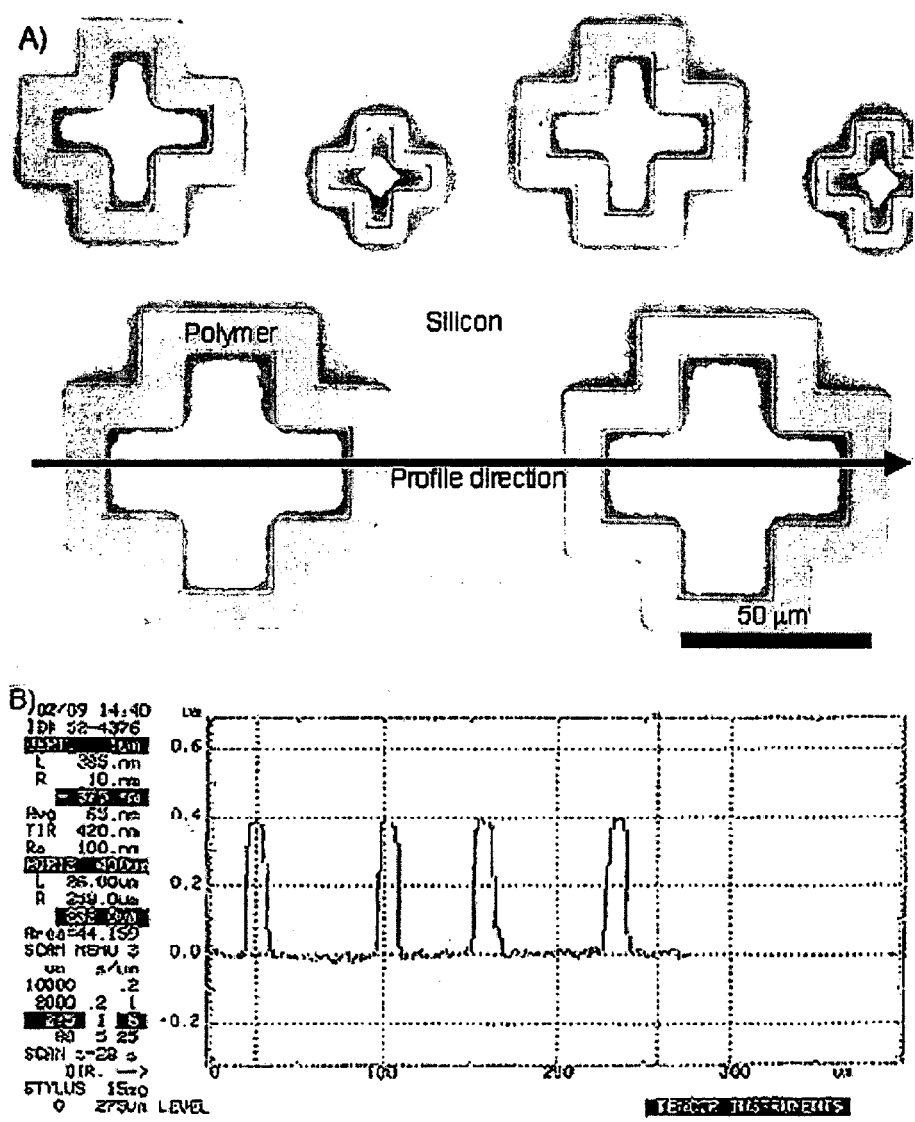
FIG. 7A is a photomicrograph of a patterning of an environmentally sensitive hydrogel in the form of plus (+) signs onto a silicon substrate via a method in accordance with the present invention.
FIG. 7B is a profilemetry graph for the path indicated by an arrow in FIG. 7A. Height of the pattern is shown to be 375 nm, while the line width of a smallest plus sign is 3 µm.
Figure 8:
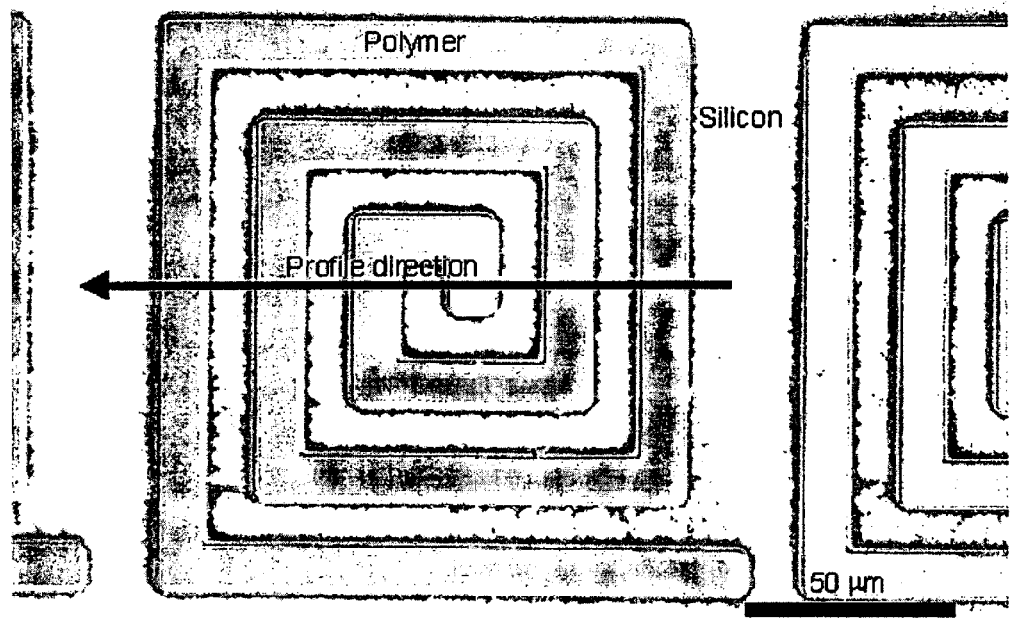
FIG. 8A is a photomicrograph of a patterning of an environmentally sensitive hydrogel in the form of a spiral onto a silicon substrate via a method in accordance with the present invention.
FIG. 8B is a profilemetry graph for the path indicated by an arrow in FIG. 8A. Height of the pattern is shown to be 450 nm.
Figure 8:
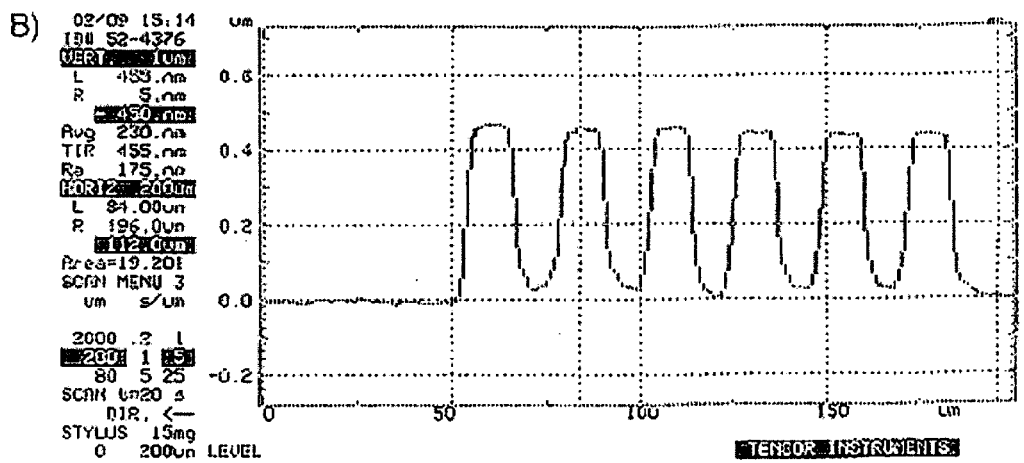
Figure 9:
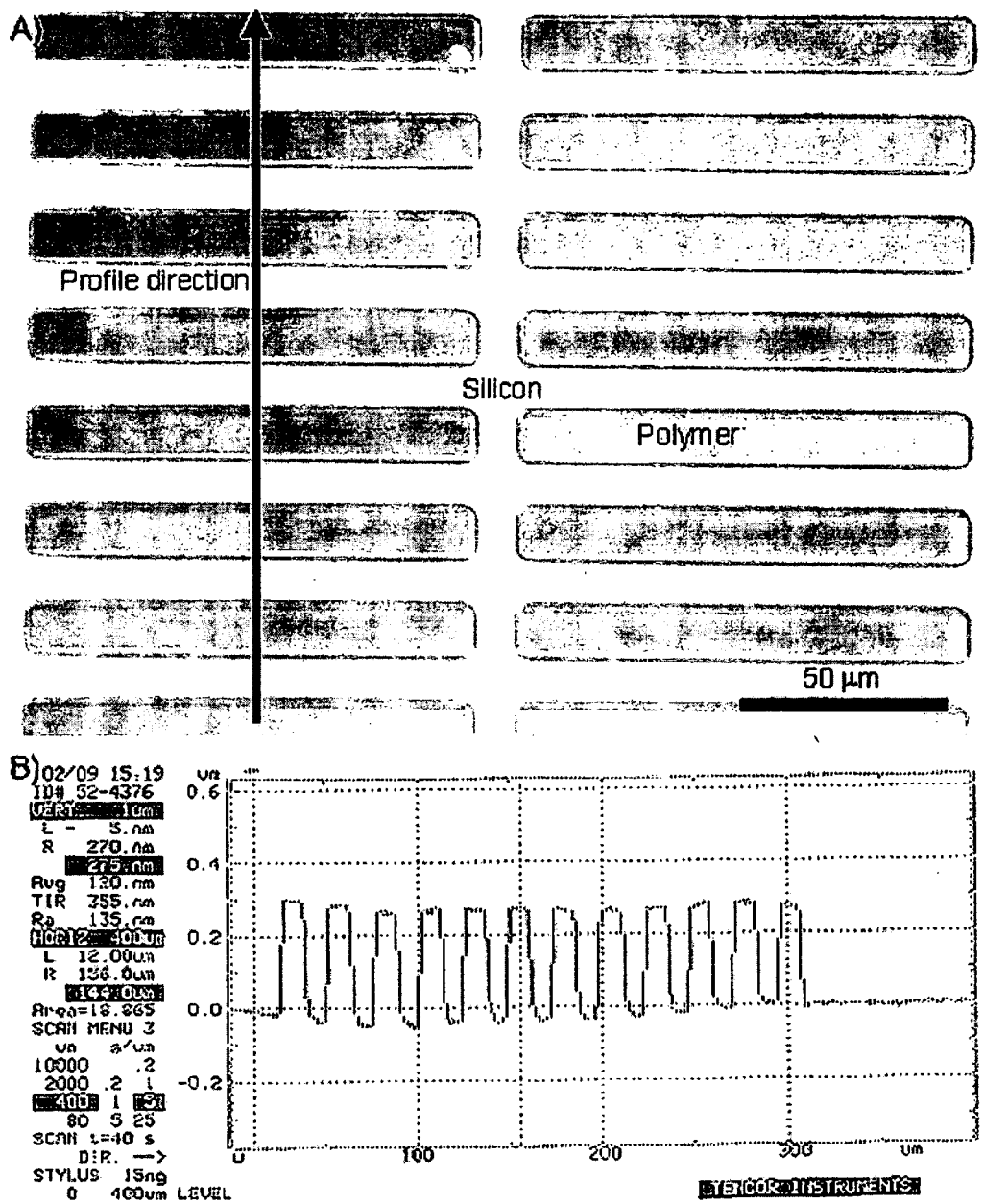
FIG. 9A is a photomicrograph of a patterning of an environmentally sensitive hydrogel in the form of bars onto a silicon substrate via a method in accordance with the present invention.
FIG. 9B is a profilemetry graph for the path indicated by an arrow in FIG. 9A. Height of the pattern is shown to be 275 nm.
Figure 10:
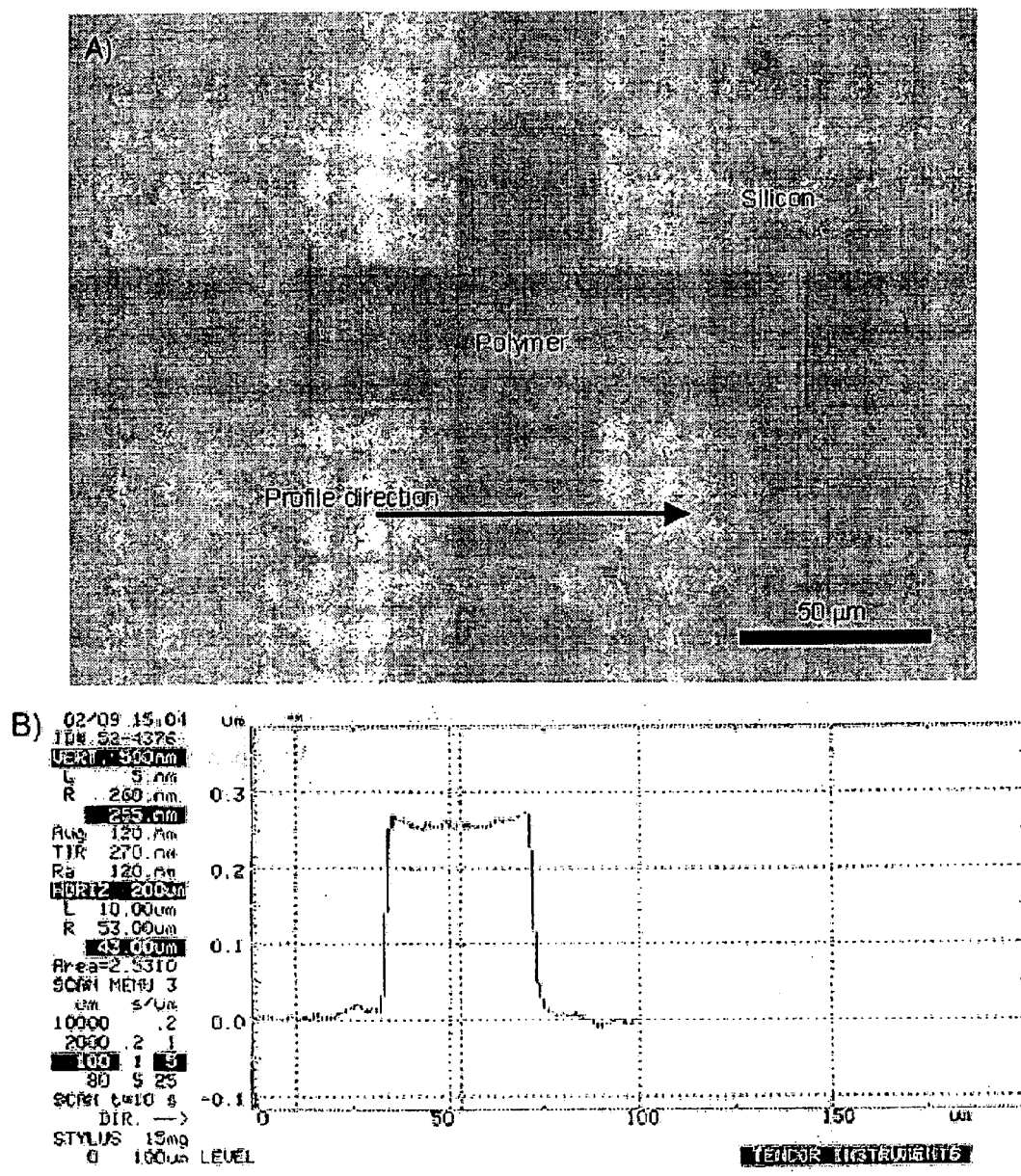
FIG. 10A is a photomicrograph of a patterning of an environmentally sensitive hydrogel in the form of a cross onto a silicon substrate via a method in accordance with the present invention.
FIG. 10B is a profilemetry graph for the path indicated by an arrow in FIG. 10A. Height of the pattern is shown to be 255 nm.
Figure 11:
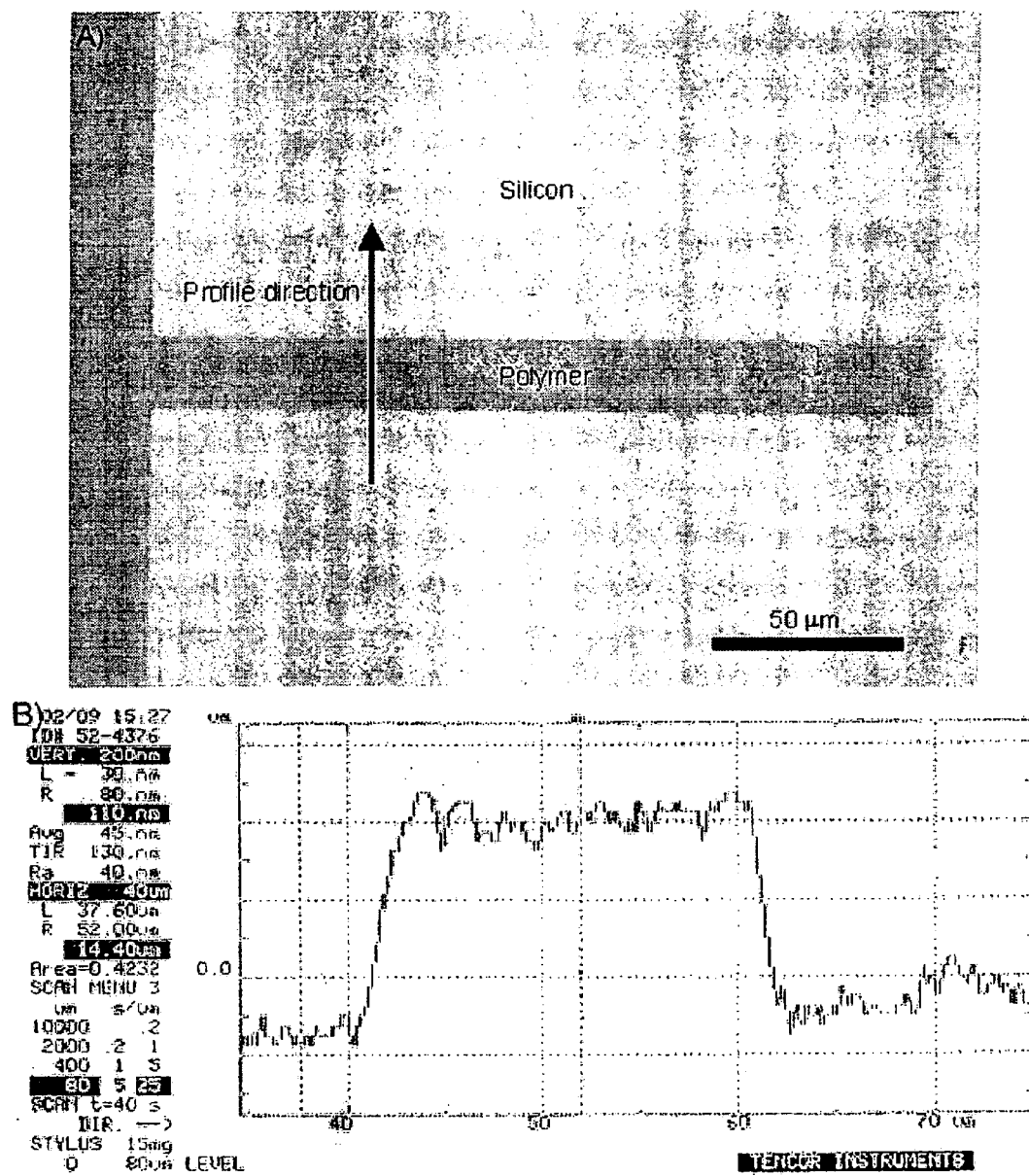
FIG. 11A is a photomicrograph of a patterning of an environmentally sensitive hydrogel in the form of a microcantilever onto a silicon subtrate via a method in accordance with the present invention.
FIG. 11B is a profilemetry graph for the path indicated by an arrow in FIG. 11A. Height of the pattern is shown to be 110 nm.

The monomer mixtures were prepared with a mole ratio of 80:20 MAA:PEGnDMA (n=200) and containing between 1 and 10 wt % DMPA. The monomer mixture was pipetted between two clamped glass slides with a Teflon® template spacer that was 0.079 cm thick, as shown in FIG. 6. Next, the glass slide assembly was placed under a UV source (EFOS Acticure™ Ultraviolet/Visible Spot Cure System) and exposed to UV light with an intensity of 23.0 mW/cm$^2$ for 1 minute to initiate the free-radical polymerization in air. The template allowed for the preparation of disc shaped polymer films with a diameter of approximately 19.3 mm. The polymer discs were then removed and washed for several days in deionized water to remove any unreacted monomer. It is important to note that the monomer samples were not bubbled with nitrogen and were not polymerized under a nitrogen environment to mimic as closely as possible the preparation of the micropatterned polymer samples.

Equilibrium swelling characteristics were obtained by exposing the polymer discs to solutions of different pH and measuring their swelling ratio. The polymer discs were soaked in citric acid and disodium phosphate buffer solutions that had pH values between 3.0 and 8.0. A water bath was utilized to keep samples at a constant temperature of 19° C. The polymer samples were soaked in each pH solution for 24 hours to allow for equilibration.

The above example illustrates a method for micropatterning thin films of environmentally sensitive hydrogels onto silicon substrates. The method overcomes the oxygen inhibition of polymerization and gaining adhesion between the silicon and micropatterned polymer. In the above example, PMAA cross-linked with PEG200DMA (20mole %) was examined. The adhesion between the silicon and polymer was achieved through the use of an organosilane agent, γ-MPS. Qualitatively, the surface modification was observed using two methods. First, water beaded up on the silicon wafer treated with the organosilane agent, while water wet the surface of the untreated silicon wafer. This was verification that the surface had been modified and had become hydrophobic, which was expected with the replacement of hydroxyl groups with carbon double bonds. In addition, a study was done where a thin polymer film was polymerized onto a silicon wafer treated with the organosilane agent and one that was untreated. In the untreated sample, the polymer peeled-off once soaked in water, while the polymer stayed adhered for days to the silicon of the treated sample. These two results confirmed that the organosilane agent acted as a bridge in bonding the silicon and polymer.

Thin micropatterns are created using the process of the above-described example by bringing the photomask into direct contact with the monomer coated substrate. This reduces somewhat the level of control over the polymer film thickness because the monomer solution's low viscosity allows for it to be easily displaced by the contacting mask. On the other hand, the photomask creates a critical barrier for the diffusion of oxygen into the film during polymerization, thus allowing for thin film polymerization. The hydrogel polymer is applied either by spin coating at 2000 rpm or spray coating and then brought in contact with the mask and exposed to UV light for 2 minutes. These conditions are successful in creating thin micropatterned polymer features with sharp edges.

Figure 12:
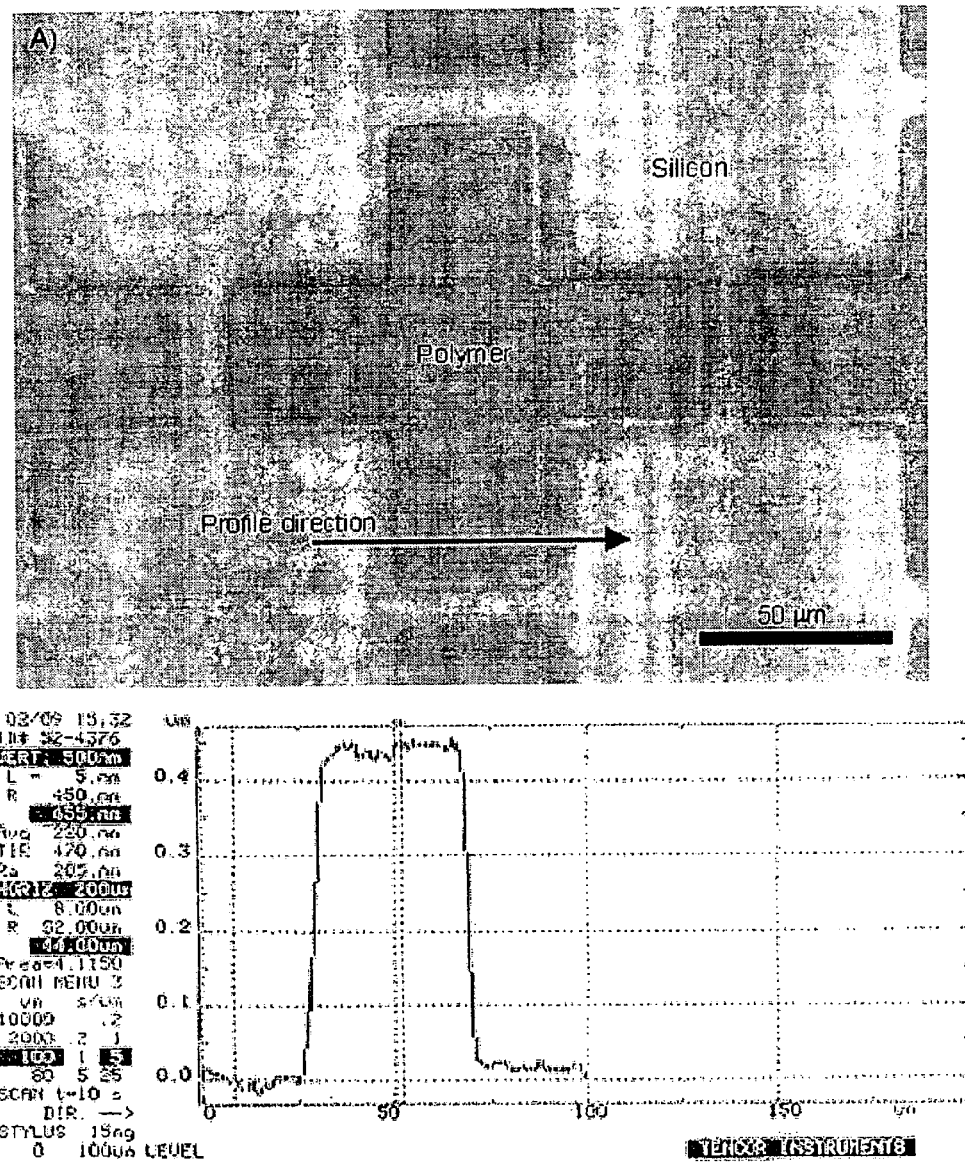
FIG. 12A is a photomicrograph of a patterning of an environmentally sensitive hydrogel in the form of a cross onto a silicon substrate via a method in accordance with the present invention.
FIG. 12B is a profilemetry graph for the path indicated by an arrow in FIG. 12A. Height of the pattern is shown to be 455 nm.
Figure 13:
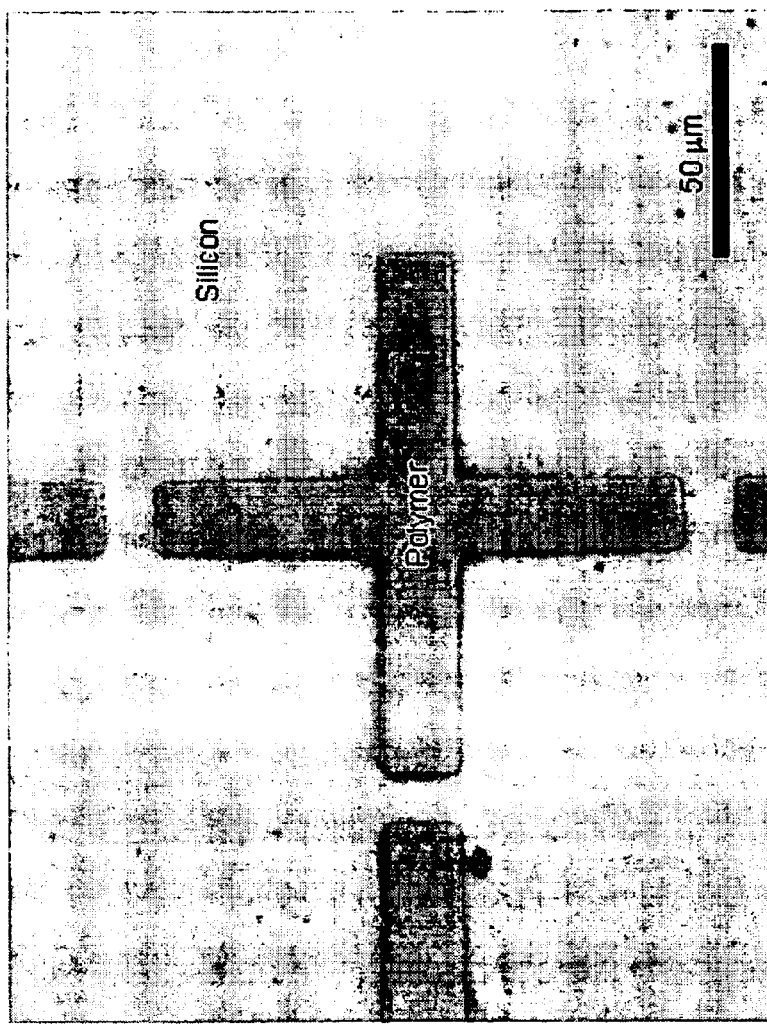
FIG. 13 is a photomicrograph of a patterning of an environmentally sensitive hydrogel in the form of a cross onto a silicon subtrate via a method in accordance with the present invention. A profilemetry scan indicated that the thickness of the pattern is approximately 400 nm.
Figure 14:
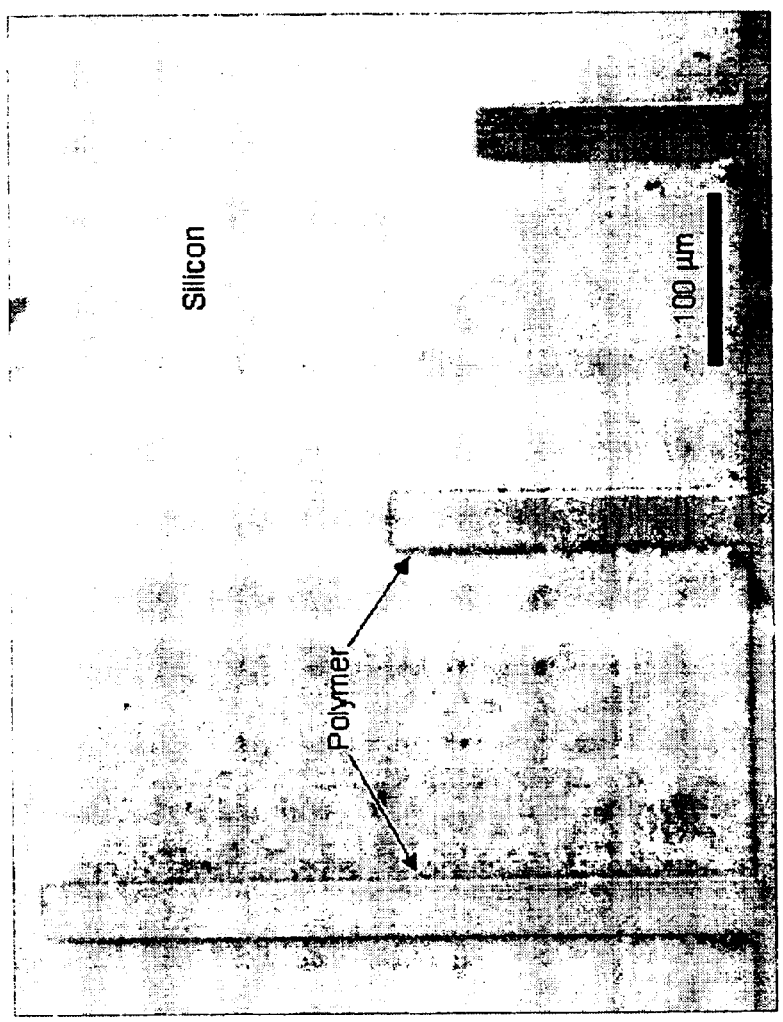
FIG. 14 is a photomicrograph of a patterning of an environmentally sensitive hydrogel in the form of microcantilevers onto a silicon subtrate via a method in accordance with the present invention. A profilemetry scan indicated that the thickness of the pattern is approximately 655 nm.
Figure 15:
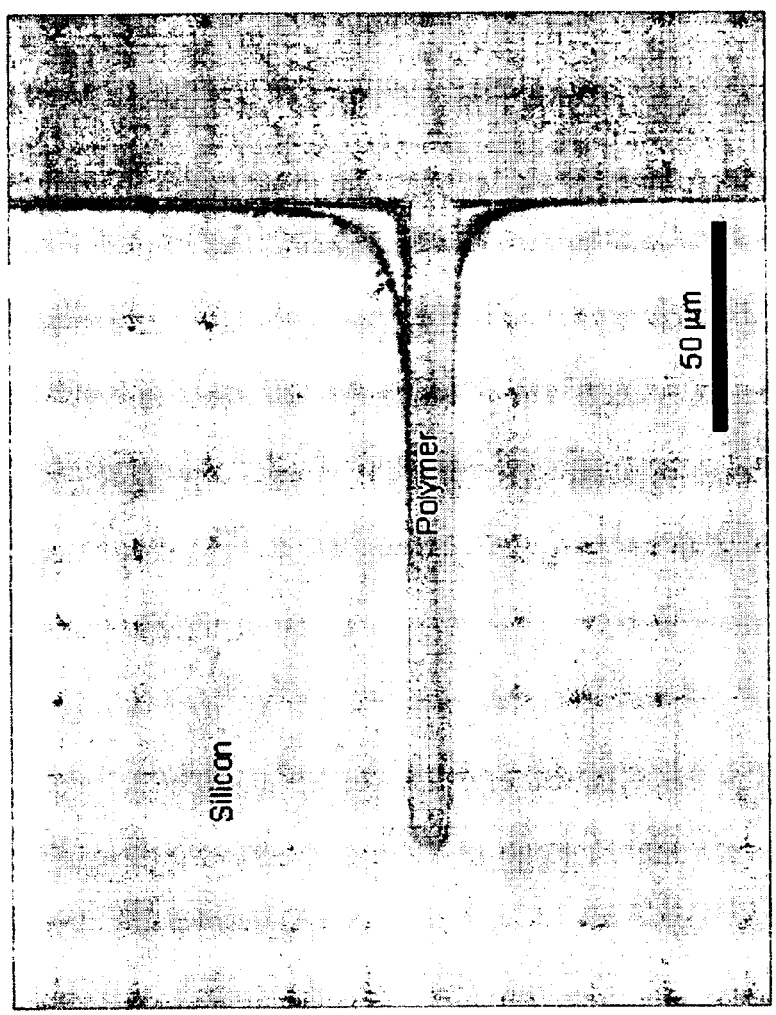
FIG. 15 is a photomicrograph of a patterning of an environmentally sensitive hydrogel also in the form of a microcantilever onto a silicon subtrate via a method in accordance with the present invention. A profilemetry scan indicated that the thickness of the pattern is approximately 690 nm.
Figure 16:
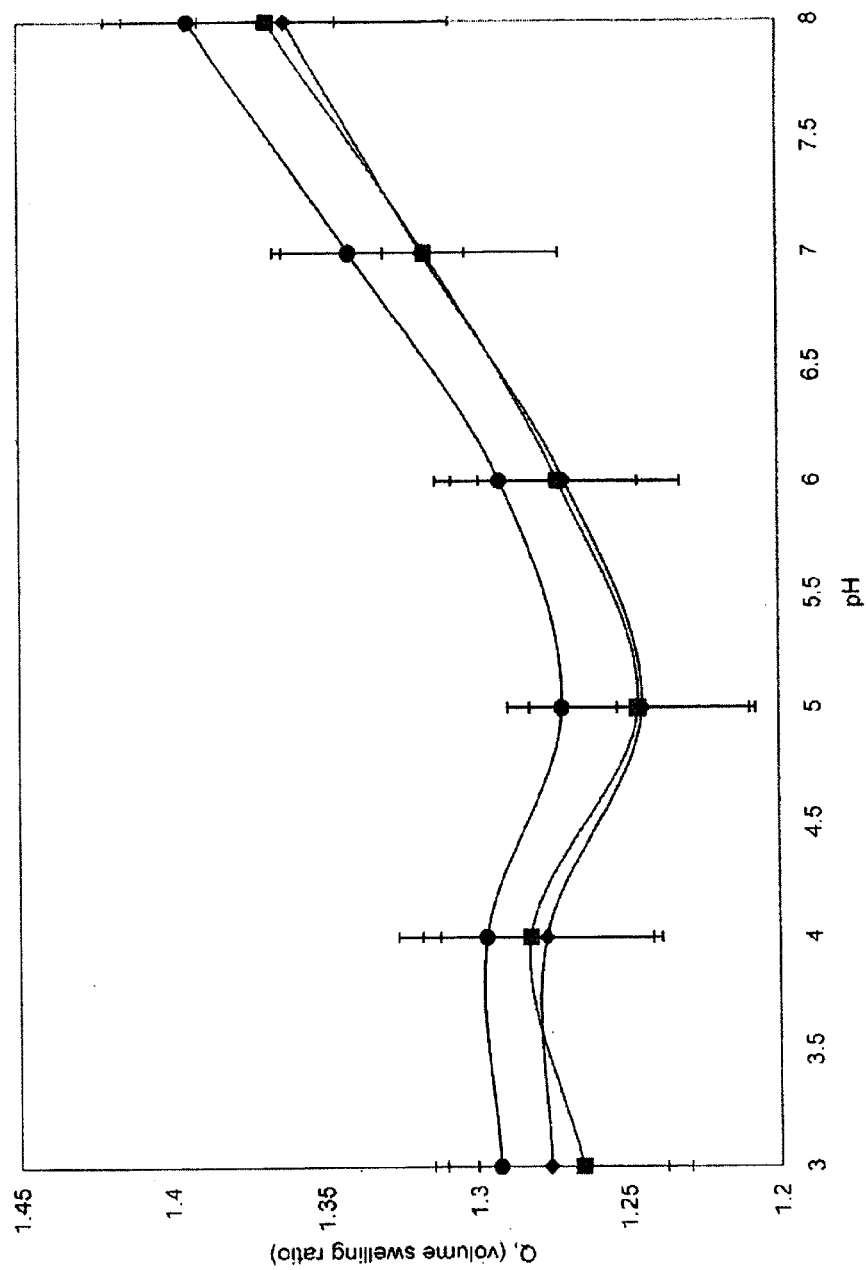
FIG. 16 is a graph of the equilibrium volumetric swelling ratio for PMAA crosslinked with wignificant amounts of PEG200DMA with different initiator concentrations. Three traces in FIG. 16 are for 1% by weight (●), 5% by weight (■), and 10% by weight (◇).

FIGS. 7–11 demonstrate the results for spray coating the monomer onto the substrate, and FIGS. 12–14 represent the results for spin coating at 2000 rpm. In addition, good results were achieved for spin coating at 2000 rpm with an UV light exposure of 1 minute (see FIG. 15). All of the patterns formed were shown to have a thickness of less than 1 μm, which facilitates patterning onto a microcantilever. The minimum line width defined by the photomask utilized is 3 μm (see smallest plus sign pattern in FIG. 7), and this was successfully transferred to the substrate. Smaller line widths could have been achieved through the use of a different photomask.

MEMS Sensor: Hydrogel-Coated Microcantilever

The above-described method is used to deposit an environmentally sensitive hydrogel onto a silicon surface in a predetermined pattern for cooperating with mechanical and electrical or optical components to enable sensing of a microbiological parameter. Where the hydrogel is crosslinked poly(methacrylic acid) (PMAA) network containing significant amounts of poly(ethylene glycol) n dimethacrylate (PEGnDMA), the sensed parameter is pH. The mechanical component may be a microcantilever capable of deflection to one side or the other depending on the degree of water absorption by the hydrogel. The amount of hydration of the polymer is in turn determined in part by the pH of a liquid in which the hydrogel-coated microcantilever is disposed.

EXAMPLE

Experimental Procedure

Once a microcantilever was patterned with pH-sensitive hydrogel, the response of the patterned microcantilever to environmental pH variation was to be examined. Observation of the bending of the microcantilever with a change in pH would be proof of concept of a MEMS sensor based on a microcantilever patterned with an environmentally sensitive hydrogel.

A crosslinked poly(methacrylic acid) (PMAA) network containing significant amounts of poly(ethylene glycol) n dimethacrylate (PEGnDMA), where n is the average molecular weight of the PEG chain, exhibits a swelling dependence on environmental pH. The monomers used were methacrylic acid (MAA) and poly(ethylene glycol) dimethacrylate (PEGDMA). The initiator used for the UV free radical polymerization was 2,2-dimethoxy-2-phenyl acetophenone (DMPA), and adhesion was gained between the silicon substrate and the polymer using an organosilane coupling agent, γ-methacryloxypropyl trimethoxysilane (γ-MPS). The MAA, DMPA, and γ-MPS were purchased from Aldrich (Milwaukee, Wis.). PEGnDMA, with n=200, was obtained from Polysciences, Inc. (Warrington, Pa.). The structures of these monomers and chemicals were given in FIG. 3.

Micropatterning Polymers onto Microcantilevers

Figure 4:
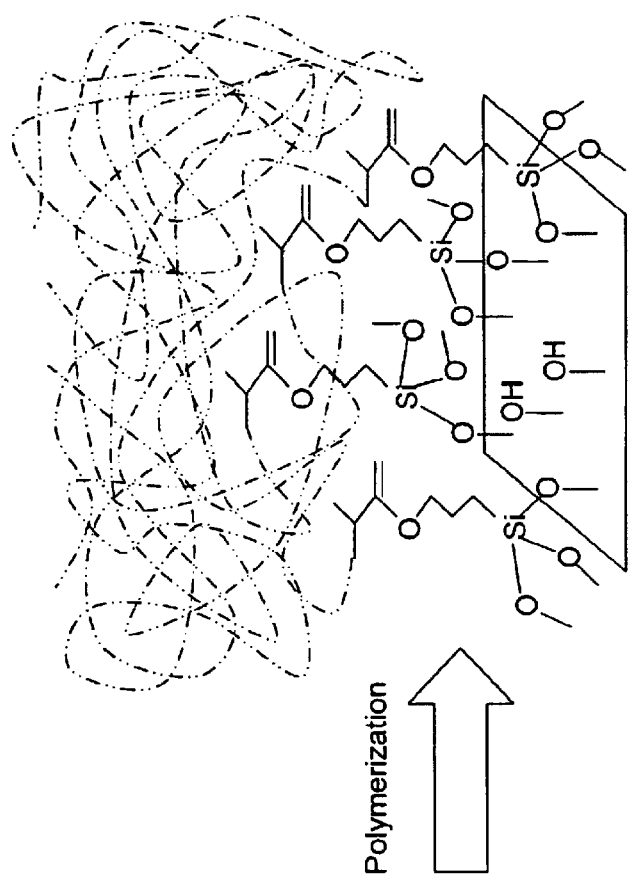
FIG. 4 is a schematic showing steps in the deposition of a hydrogel layer on a microcantilever in accordance with the present invention, more particularly showing the formation of an organosilane self-assembled monolayer and a bonding thereof with a hydrogel polymer network.
Figure 4:
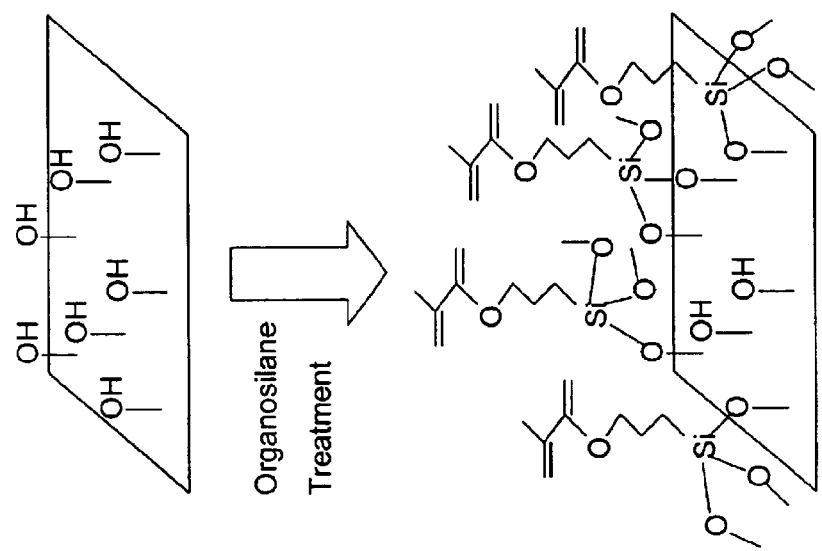

Silicon and silicon dioxide microcantilevers all having thicknesses of approximately 1 μm were fabricated in the ECE Solid State laboratories. These silicon samples containing the microcantilevers were treated with an organosilane agent, γ-MPS, to gain bonding between the silicon and polymer. The silicon pieces containing microcantilevers were soaked in a 10 wt % solution of γ-MPS in acetone for more than 2 hours. Then, these were rinsed in acetone followed by methanol, and then air-dried. Methanol was utilized as the final rinse because it is a low surface tension liquid and, thus, helps prevent the occurrence of stiction, cantilever failure by pinning to substrate when dried. As aforementioned, the organosilane coupling agent forms a self-assembled monolayer on the silicon dioxide surface and presents methacrylate pendant groups that react and bond with the polymer film. A schematic of this process is illustrated in FIG. 4.

The monomer mixtures were prepared with a mole ratio of 80:20 MAA:PEGnDMA, where n=200, and containing 10 wt % DMPA. The monomer mixture was either spray-coated or spin-coated (for 30 seconds) onto the silicon samples containing microcantilevers. Next, polymer micropatterns were created by UV free-radical polymerization using a Karl Suss MJB3 UV400 mask aligner. The Karl Suss MJB3 UV400 mask aligner enabled for alignment accuracies of 0.1 microns, which was critical for the patterning of the polymer onto the microcantilever. The photomask was fabricated at the Purdue ECE Solid State Lab. The mask is made on a photoplate purchased from Nanofilm. It is 4"×4"×0.6" low reflectance chrome on white crown substrate. After bringing the sample into contact with the mask, the sample was exposed to UV light with intensity of 23.0 mW/cm² for exposure time of 1 to 2 minutes. The sample was then removed and allowed to soak in deionized distilled water for greater than 24 hours to remove any unreacted monomer. A schematic of the procedure for micropatterning onto silicon surface was included as FIG. 5.

The critical step in the procedure for patterning the polymer onto the microcantilevers was the alignment. Previously to applying the monomer, the silicon wafer with microcantilevers was placed into the mask aligner and brought into general alignment with the photomask. Then, the sample was removed and either spin or spray coated with monomer, and then, it was repositioned into the mask aligner. Subsequently, the sample was brought in close proximity of the mask but without contacting the monomer solution. If the mask contacts the monomer solution, the monomer solution would smear and be displaced requiring the procedure to be restarted from the beginning. Therefore, the alignment was done with mask and sample in close proximity, which resulted in the mask and sample images not in focus. Once the alignment was made, the sample was brought into direct contact with the mask followed by exposure to UV light to polymerize.

The final samples of the patterned polymer were examined several ways. Three different optical microscope systems were utilized to examine the patterned microcantilevers: Microscopic I (Nikon Eclipse E600 equipped with a Kodak DC290 Zoom Digital Camera) allowing for pictures to be taken at 200×, 400× and 1000× magnification, Microscope II (Nikon Industrial Microscope Eclipse L150 equipped with a Insight Digital Camera with KAI-2000 Mosaic CCD) allowing for images to be taken with 50×, 100×, 200×, 500×, and 1000× magnification, and Microscope III (Nikon Eclipse E600 with components for fluorescent microscopy) including a 60× water immersion objective. A profilometer (alpha-step 200, Tencor Instruments, San Jose, Calif.) was also used to determine the height and profile of the pattern.

Evaluation of Polymer Patterned Microcantilevers

Figure 17:
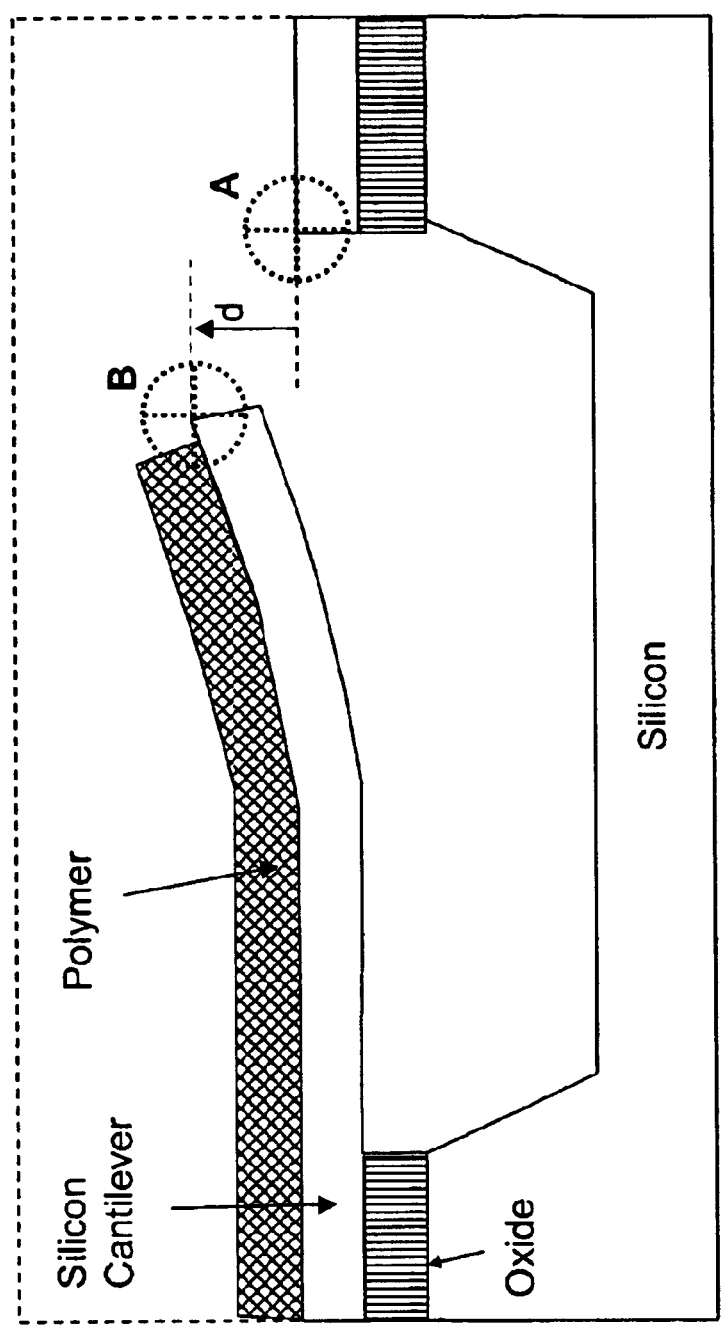
FIG. 17 is a schematic side elevational view of a microcantilever coated with a layer of hydrogel, showing a bending of the microlever under stresses from the hydrogel in a dry state.

The microcantilevers patterned with environmentally sensitive hydrogels were examined. It was observed that the patterned microcantilevers were bent up when the polymer was in the dehydrated state. Knowing that the stress on the cantilever surface is directly related to its bending (eqn. 2.2), the deflection of the cantilevers was measured using Microscope II to get an idea of the stress in the dry polymer films. This deflection measurement was made by manually adjusting the focus plane from the edge of the cantilever well (point A in FIG. 17) to the tip of the cantilever (point B in FIG. 17) and recording the change in focus values from the z-axis fine focus knob. These changes in focus values were converted to μm via calibrating by comparing a change in focus measurement with a profilometry run of an etched well. There is some inherent error in this measurement due the dependence on the human eye to observe the focus plane, but for the relatively large deflections on order of 10 μm, this method is more than sufficient for determining the deflection.

Microcantilever Bending Studies

Figure 18:
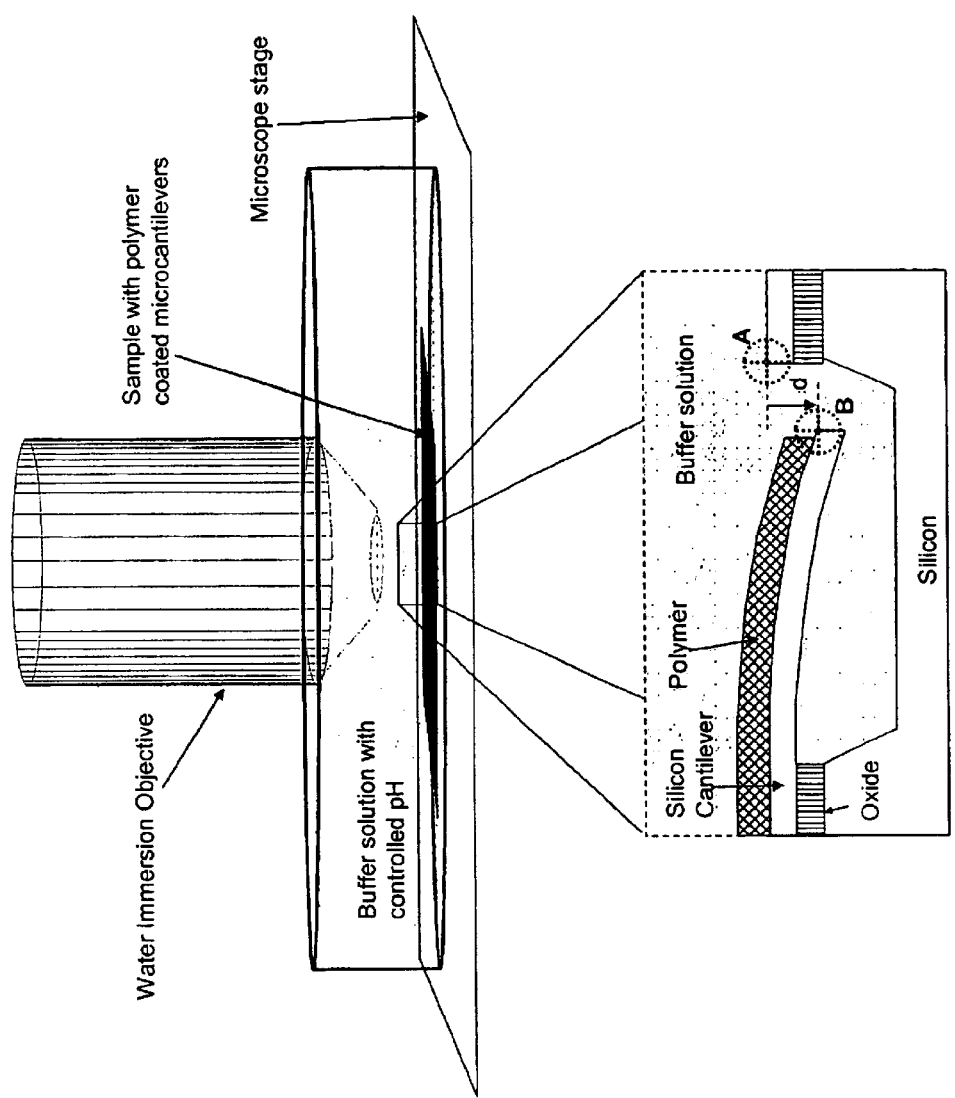
FIG. 18 is a diagram of an assembly for monitoring the deflection of a hydrogel-patterned microcantilever with variance of pH of a buffer solution. The difference in focus between plane A and plane B is utilized to calculate the deflection.

After patterning environmentally sensitive hydrogels onto microcantilevers, dynamic and equilibrium bending studies were conducted on a set of three silicon microcantilevers. The silicon wafer containing the microcantilevers patterned with polymer was placed in a petri dish that was filled with a buffer solution initially composed of mixture of 0.1 M citric acid and 0.2 M disodiumphosphate resulting in a pH of 2.81. Then, the petri dish with sample was placed onto the stage of Microscope III (see FIG. 18). A 60× water immersion objective was used to observe the sample. The sample was allowed to equilibrate at the pH for 10 minutes, and then the deflection of the cantilever was measured using the method described above. After that, the pH of the solution was increased by removing approximately 5 ml of buffer solution and replacing it with 5 ml of 0.2 M disodiumphosphate. The pH of the solution was measured using a handheld pH meter with micro pH probe (IQ Scientific Instruments, Inc., San Diego, Calif.). After the pH was increased, the deflection of one polymer patterned cantilever was monitored every minute to observe the dynamic response.

Results

In the above-described example, thin films of environmentally sensitive hydrogels were deposited in patterns onto microcantilevers. In addition, the bending of the patterned microcantilevers was examined as a function of pH. The environmentally sensitive hydrogel examined was PMAA cross-linked with PEG200DMA (20 mole %); this gel exhibits a swelling dependence on pH.

Patterning Microcantilevers

Figure 19:
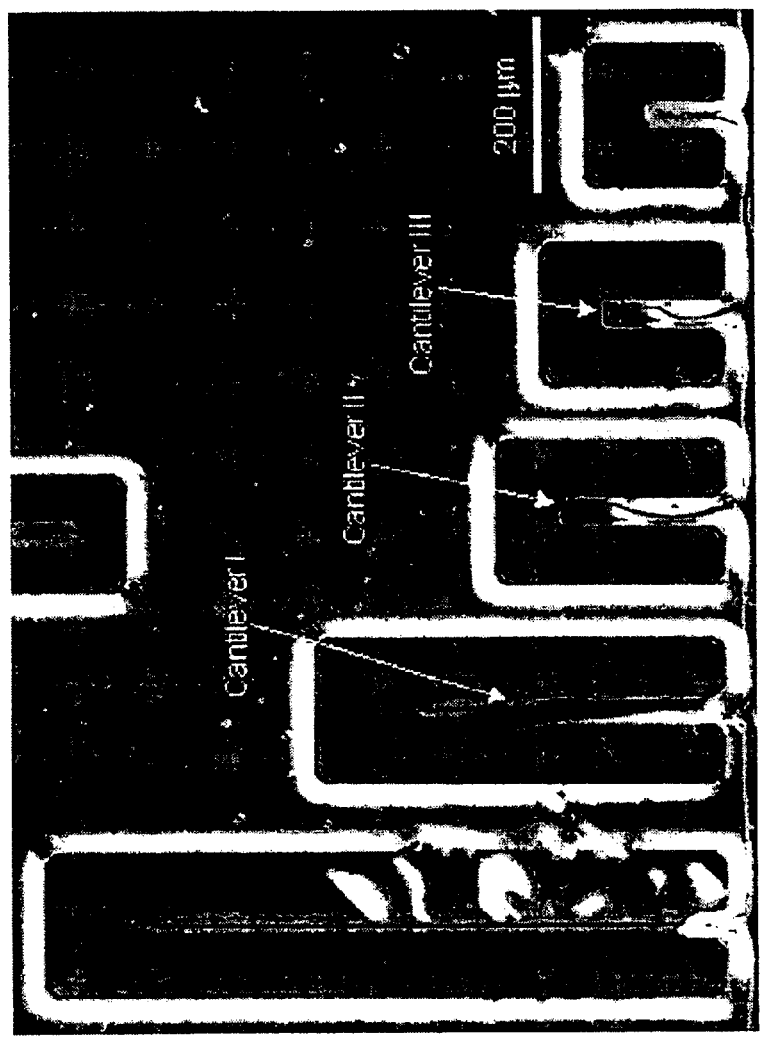
FIG. 19 is a photomicrograph, taken with Microscope II in Nomarski mode, of a set of silicon microcantilevers patterned with an environmentally sensitve hydrogel in accordance with the invention. A profilemetry scan indicated that the thickness of the patterned hydrogel was approximately 2.5 µm.
Figure 20:
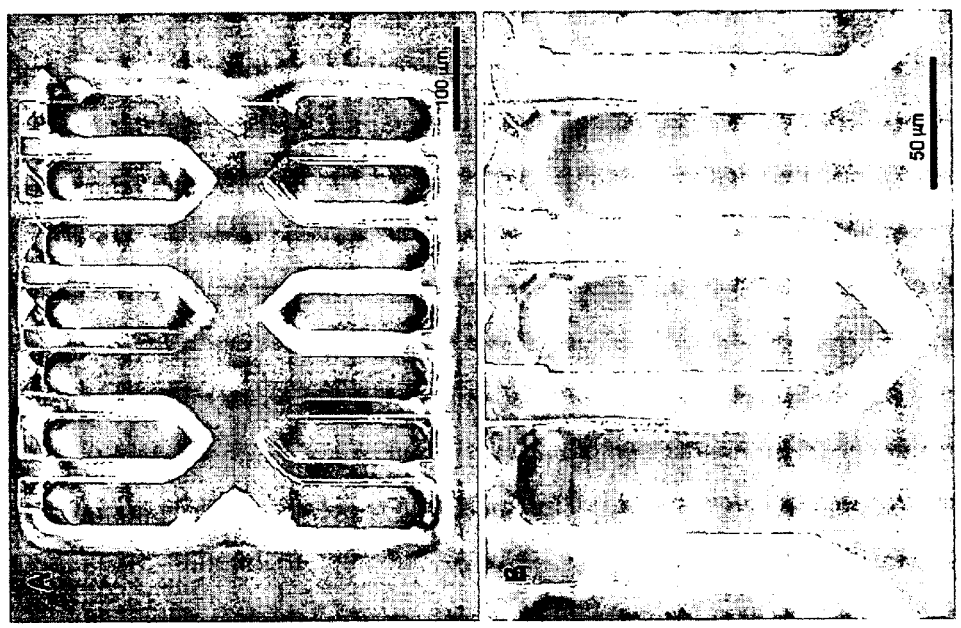
FIGS. 20A and 20B are photomicrographs, taken with Microscope II in Nomarski mode at magnifications of 200× and 500×, of a another set of silicon microcantilevers patterned with an environmentally sensitve hydrogel in accordance with the invention. A profilemetry scan indicated that the thickness of the patterned hydrogel was approximately 2.8 µm.
Figure 21:
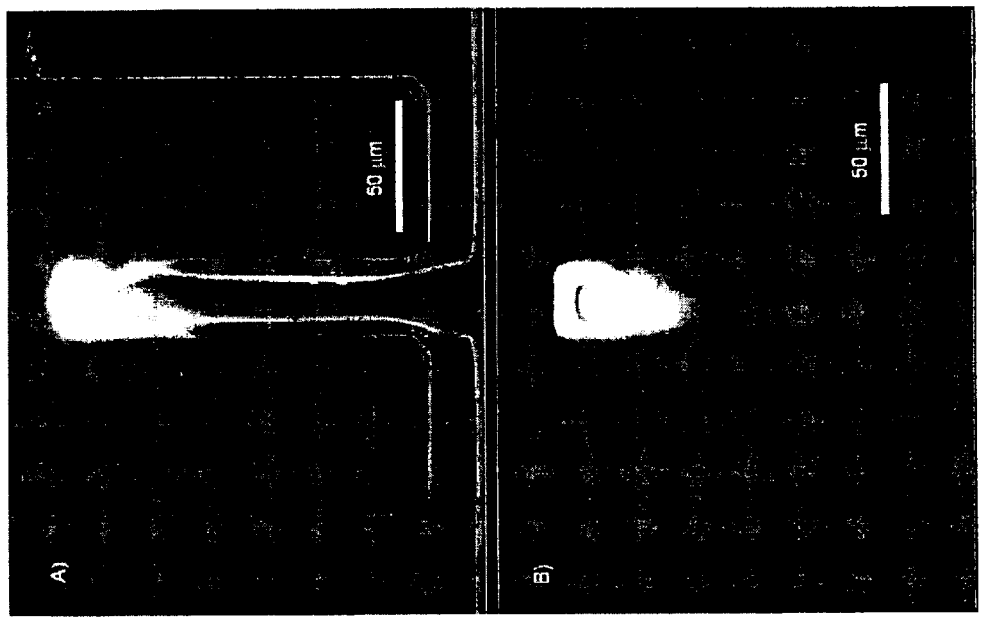
FIGS. 21A and 21B are photomicrographs of a microcantilever (Cantilever III in FIG. 19) provided with a layer of hydrogel with the focus on the substrate and on the cantilever tip, respectively. The image was captured with a Microscope II in Nomarski mode.
Figure 22:
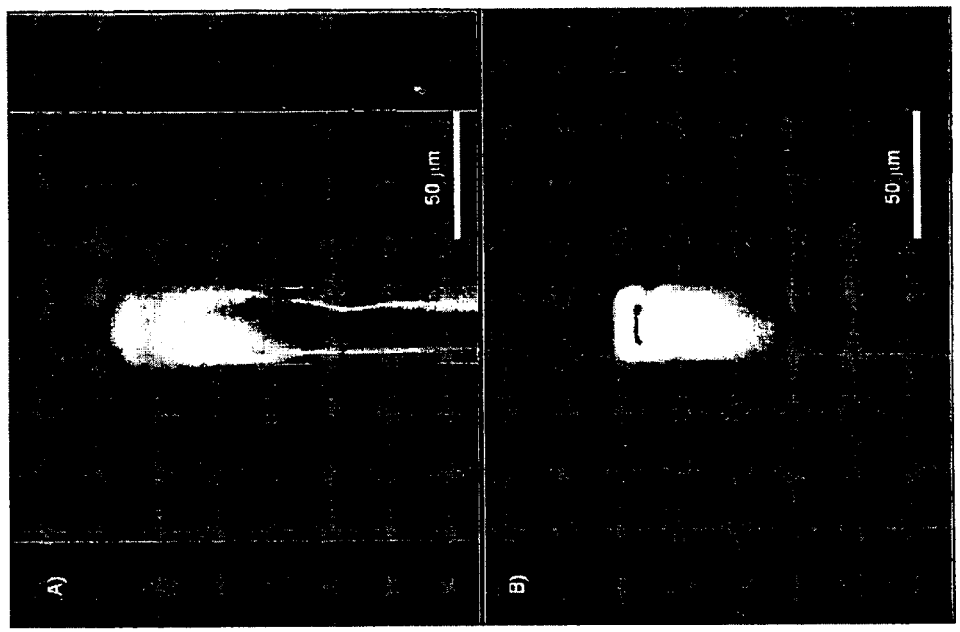
FIGS. 22A and 22B are photomicrographs of another microcantilever (Cantilever II in FIG. 19) provided with a layer of hydrogel with the focus on the substrate and on the cantilever tip, respectively. The image was captured with a Microscope II in Nomarski mode.
Figure 23:
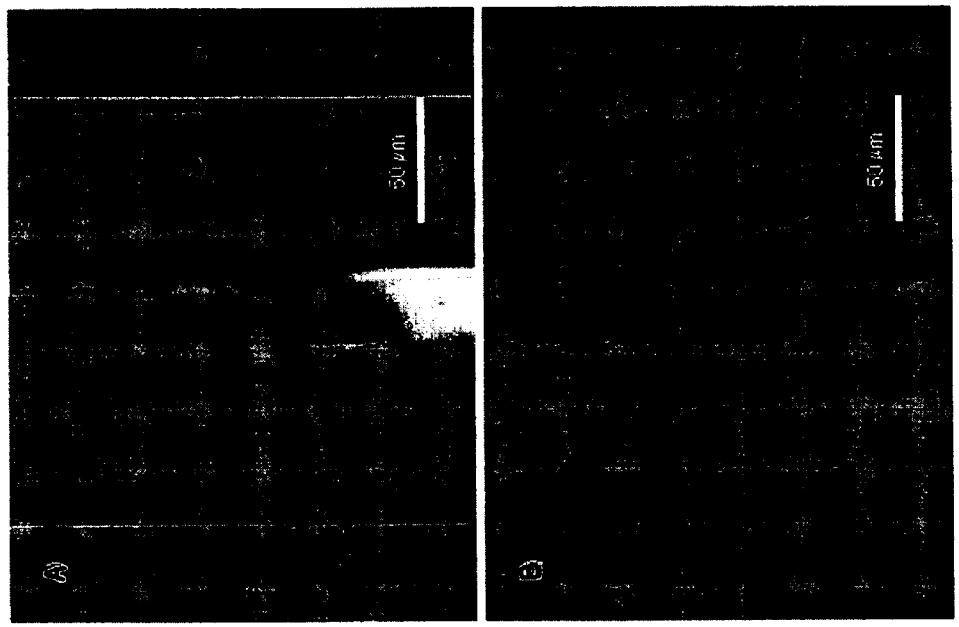
FIGS. 23A and 23B are photomicrographs of yet another microcantilever (Cantilever I in FIG. 19) provided with a layer of hydrogel with the focus on the substrate and on the cantilever tip, respectively. The image was captured with a Microscope II in Nomarski mode.
Figure 24:
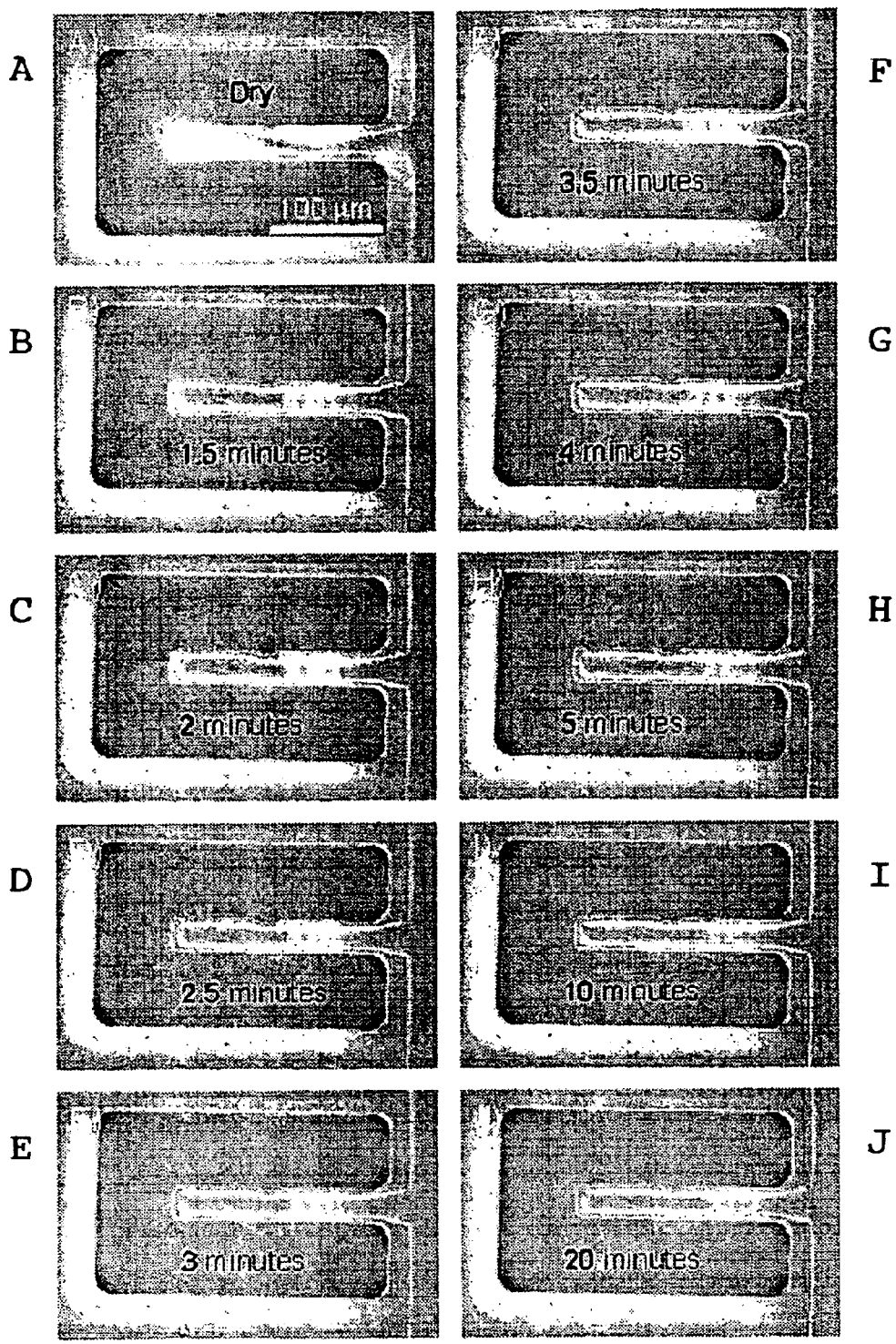
FIGS. 24A through 24J are photomicrographs, with a constant focus on the substrate, of the hydrogel-patterned microcantilever of FIGS. 22A and 22B, taken at indicated times after an immersion of the microcantilever in water.

In patterning microcantilevers, the alignment of the photomask with the microcantilevers is critical. With sufficient alignment, environmentally sensitive hydrogels were successfully patterned onto silicon microcantilevers (see FIGS. 19 and 20). In this sample, the monomer was applied by spin coating at 2000 rpm. Once aligned in the mask aligner, the sample was brought into contact with the photomask and exposed to UV light for 1 minute. These conditions proved to be successful in creating thin polymer features patterned onto silicon microcantilevers and demonstrated the ability to precisely pattern environmentally sensitive hydrogels onto microcantilevers. The thickness of the polymer film patterned on the microcantilevers was determined to be approximately 2.5 $\mu$m using profilometry. The bending characteristics of three of the microcantilevers were also examined (cantilever I, cantilever II, and cantilever III, all with widths of 29.3 $\mu$m, thicknesses of approximately 800 nm, and lengths of 380 $\mu$m, 184.5 $\mu$m, and 134.4 $\mu$m, as shown in FIG. 19).

Microcantilever Bending as a Result of Hydration

During polymerization, the volume of the polymer system shrinks due to the chemical bonds broken and formed and the new configuration that is adopted by the created linkages [Wen, M., L. E. Scriven, and A. V. McCormick. Differential scanning calorimetry and cantilever deflection studies of polymerization kinetics and stress in ultraviolet curing of multifunctional (meth)acrylate coatings. Macromolecules, 35, 112–120 (2002). Because as the polymer film was forming it adhered to the silicon substrate via the organosilane coupling agent, the film was inhibited from shrinking where it was bond to the cantilever surface. This resulted in stress being generated within the film. The patterned microcantilevers that are shown in FIG. 19 were bent up due to the action of this stress within the polymer film on the surface of the microcantilever. FIGS. 21A, 21B through 23A, 23B further demonstrate the stress induced bending of the microcantilevers. The magnitude of this bending in the dry state was measured using an optical microscope. The measured deflections were 17 $\mu$m, 22 $\mu$m, and 51 $\mu$m for the cantilevers of FIGS. 21A, 21B; 22A, 22B, and 23A, 23B, respectively.

The hydration process of the patterned cantilever beams was observed using an optical microscope. The set-up was similar to that depicted in FIG. 18, except Microscope I and a 40× objective were utilized. The sample was immersed in water and then was monitored. A series of images were taken of Cantilever II during swelling; these images are shown as FIGS. 24A–24J. As the polymer film absorbed water, the network swelled and the cantilever bent back to level with the silicon substrate. When level with the substrate, the stress on the top surface of the cantilever is equal to the stress on the bottom surface. Therefore, it can be implied that the polymer film has relaxed the stress at the surface of the cantilever. As can be seen in FIGS. 24A–24J, the swelling of the thin polymer film was completed within a few minutes.

Microcantilever Bending with pH Variation

Figure 25:
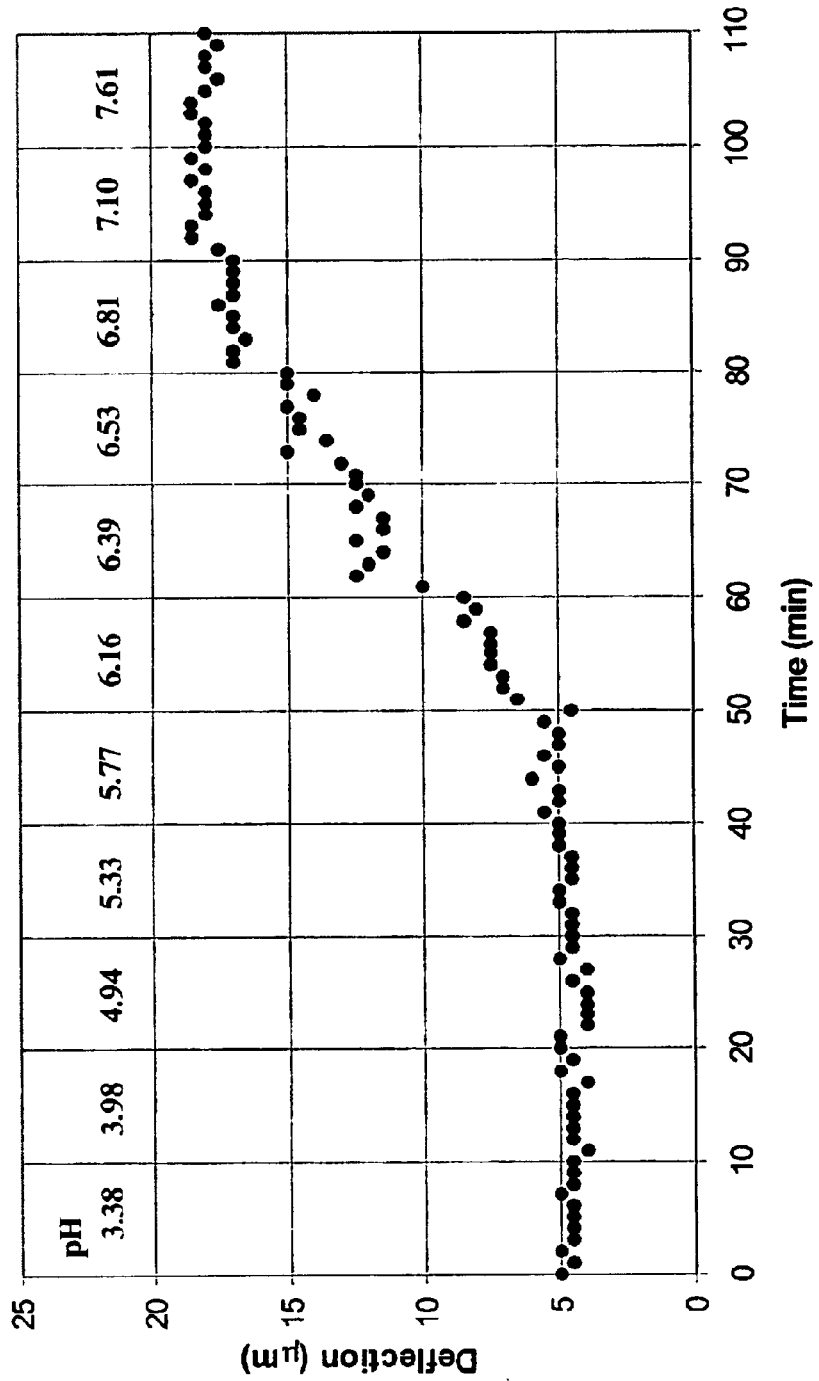
FIG. 25 is a graph showing a dynamic swelling response of the cantilever of FIGS. 19, 23A and 23B, with a length of 380 μm, with varying pH response.
Figure 26:
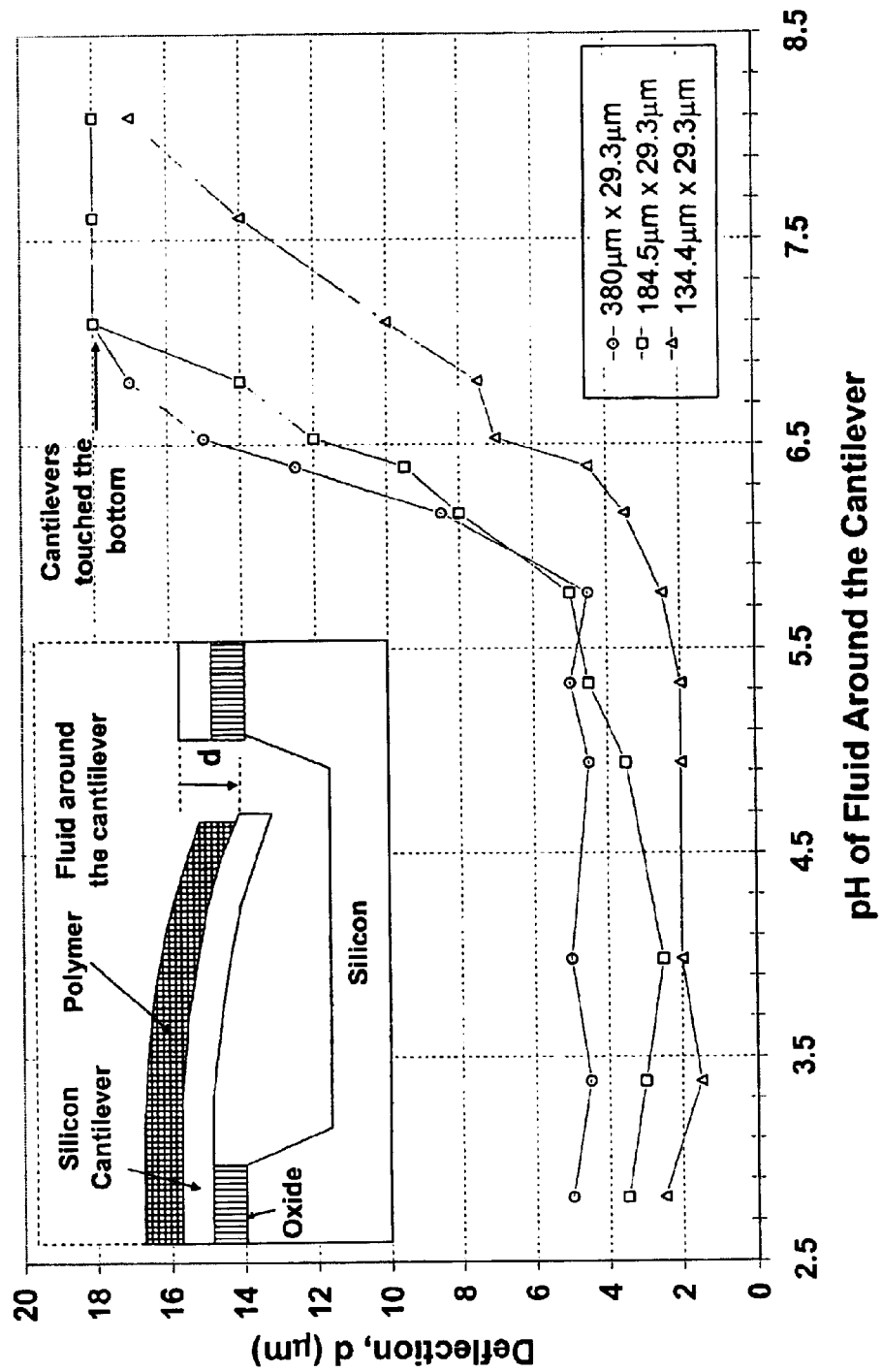
FIG. 26 is a graph showing an equilibrium swelling response of cantilevers of FIG. 19.

The patterned microcantilevers' dynamic and equilibrium bending characteristics with variances in environmental pH were examined. The three patterned cantilevers shown in FIG. 19 were monitored while exposed to buffer solutions of varying pH. FIG. 25 demonstrates the dynamic response of cantilever I and shows that the response to the change in pH is rapid. The equilibrium bending of all three cantilevers was measured and is included in FIG. 26. These were exceptional results demonstrating that the micropatterned thin hydrogel film was capable of sensing the change in environmental pH, and then, swell in response resulting in actuation of the microcantilever.

This response can be tailored via a number of ways, including by varying the swelling properties of the polymer and changing the dimensions of the cantilever. For instance, some examples of how the swelling properties of the polymer can be tailored include adjusting the amount of crosslinking, the length of the crosslinker, or changing the monomers used. In addition, Stoney's equation (eqn. 2.2) illustrates that the deflection is inversely proportional to the thickness of the cantilever squared and directly proportional to the length of the cantilever squared. Thus, by adjusting these parameters, the response can be tailored. This is demonstrated in FIG. 26, where the response was different for cantilevers of different lengths. The aforementioned parameters allow for the sensing response to be tailored for the desired operating range and sensitivity.

The methods developed here can be extended to other environmentally sensitive hydrogels enabling the fabrication of a variety of MEMS sensors.

MEMS Apparatus

Figure 27:
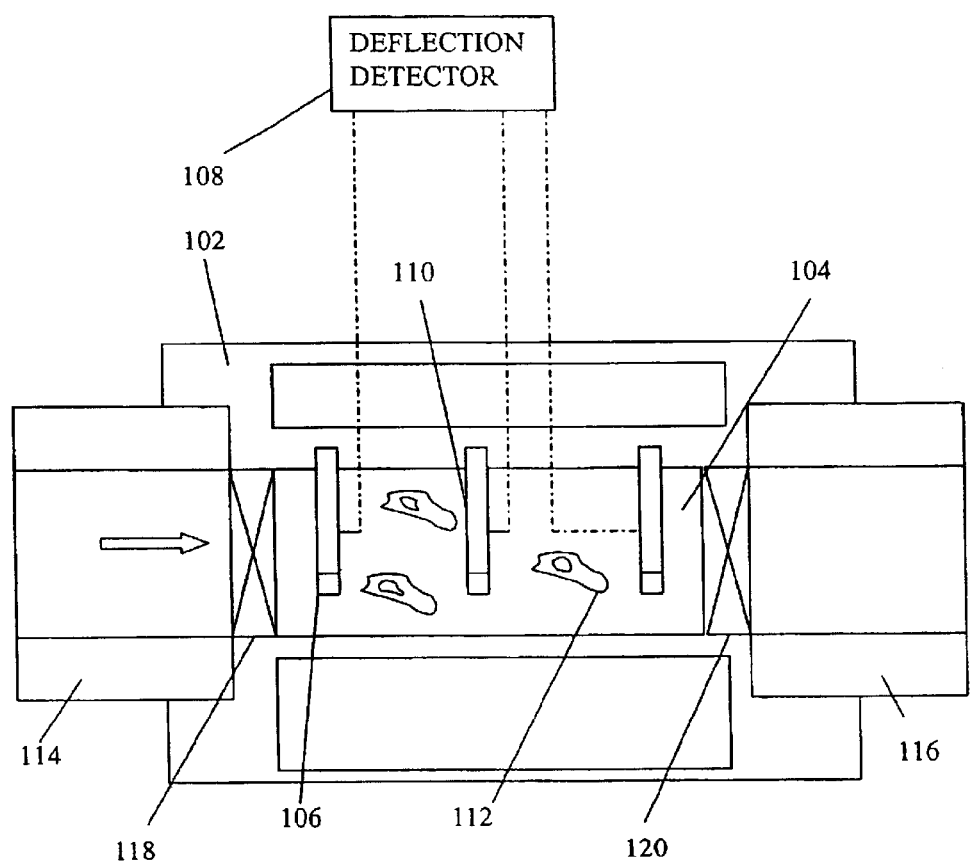
FIG. 27 is a diagram of a monitoring apparatus useful in detecting viability of biological cells, in accordance with a feature of the present invention.

As illustrated in FIG. 27, a monitoring apparatus useful in detecting viability of biological cells comprises a substrate 102 defining a microscopic chamber 104. Three microcantilevers 106 extend from substrate 102 into chamber 104. A detector 108 is operatively connected to microcantilevers 106 for sensing a state of deformation thereof. Each microcantilever 106 is provided on an upper surface, as discussed above, with a layer 110 of an environmentally sensitive hydrogel polymer having a configuration which changes in accordance with presence and absence of an environmental parameter.

A liquid containing biological cells 112 to be assayed for viability is fed into chamber 104 via a microbore inlet tube 114. A microbore outlet tube 116 may communicate with chamber 104 for siphoning off a sample liquid after testing has been completed. Electric, mechanical or electromechanical micro-valves 118 and 120 may be provided in operative relationship to inlet tube 114 and outlet tube 116, respectively, as well as chamber 104, for controlling the liquid flow through the chamber to effectuate temporary capture of a liquid sample and subsequent siphoning off of the liquid sample after testing has been completed, whereby biological cells are captured and concentrated to minimize a detection time.

Detector 108 may be a resistive circuit with a piezoelectric element where a change in voltage drop across the piezoelectric element or a change in current through the piezoelectric element indicates a deformation thereof. Alternatively, as discussed above, detector 108 may be an optical assembly wherein a laser beam is reflected from each cantilever 106 to a sensor such as a charge coupled device CCD. Movement of the beam across the optically sensitive surface of the CCD is indicative of deflection of the monitored microcantilever 106. In another alternative implementation, detector 108 is a resonant circuit with a frequency detector. The resonant frequency of the circuit changes with any stress exerted on the respective microcantilever owing to conformational changes in the respective hydrogel layer.

As discussed above, the hydrogel layer may be responsive to a chemical species such as hydrogen ion or an analyte such as glucose. Where the hydrogel polymer is responsive to pH, the hydrogel is a cross-linked network of hydrophilic monomers preferably taken from the group consisting of unsaturated organic acid monomers, acrylic substituted alcohols, and acrylamides. More particularly, the monomers are taken from the group consisting of methacrylic acids, acrylic acids, glycerolacrylate, glycerolmethacrylate, 2-hydroxyethylmethacrylate, 2-hydroxyethylacrylate, 2-(dimethylaminoethyl methacrylate, N-vinyl pyrrolidone, methacrylamide, and N,N-dimethylacrylamide poly (methacrylic acid) containing amounts of poly(ethylene glycol) n dimethacrylate, where n is the average molecular weight of the PEG chain. In the last case, the average molecular weight of the PEG chain is preferably between about 50 and about 500 and more preferably about 200.

Where the chemical species is glucose, the hydrogel polymer may take the form of a boronate-containing polymer complex that swells due to diffusion of ion species upon chemical responsiveness when in contact with glucose.

The environmental parameter may be temperature. In that case the hydrogel polymer may be poly(N-isopropylacrylamide) (PNIAAm) or may be alternatively obtained by polymerizing in an aqueous solution, N-alkyl acrylamide derivatives with acrylic acid, alkali metal salts of acrylic acid, or mixtures thereof, and diacetone acrylamide.

Although the invention has been described in terms of particular embodiments and applications, one of ordinary skill in the art, in light of this teaching, can generate additional embodiments and modifications without departing from the spirit of or exceeding the scope of the claimed invention. For instance, it may be desirable in some application to provide hydrogel polymers on opposing sides of a microcantilever. The opposing layers may be sensitive to different environmental parameters, such as temperature and pH, and arranged so that the presence of cellular metabolic activity will result in a bending of the microcantilever in the same direction, regardless of which environmental parameter is being sensed. Accordingly, it is to be understood that the drawings and descriptions herein are proffered by way of example to facilitate comprehension of the invention and should not be construed to limit the scope thereof.

What is claimed is:

1. An apparatus useful in detecting viability and metabolic activity of biological cells, comprising
    a substrate defining a microscopic chamber;
    at least two valves disposed in operative relationship to said chamber for controlling fluid flowthrough said chamber to effectuate temporary capture of a liquid sample and subsequent siphoning off of said liquid sample after testing has been completed, whereby biological cells are captured and concentrated to minimize a detection time;
    at least one microcantilever connected to said substrate and extending into said chamber;
    a detector device operatively connected to said microcantilever for sensing a state of deformation thereof; and
    a layer of an environmentally sensitive hydrogel polymer provided on at least one surface of said microcantilever, said hydrogel polymer having a configuration changing in accordance with presence and absence of an environmental parameter.

2. The apparatus defined in claim 1 wherein said environmental parameter is a chemical species.

3. The apparatus defined in claim 2 wherein said chemical species is the hydrogen ion, the state of deflection of said microcantilever being indicative of the pH of said liquid.

4. The apparatus defined in claim 3 wherein said hydrogel polymer is a cross-linked network of hydrophilic monomers taken from the group consisting of methacrylic acids, acrylic acids, glycerolacrylate, glycerolmethacrylate, 2-hydroxyethylmethacrylate, 2-hydroxyethylacrylate, 2-(dimethylaminoethyl methacrylate, N-vinyl pyrrolidone, methacrylamnide, and N,N-dimethylacrylamide poly (methacrylic acid) containing amounts of poly(ethylene glycol) n dimethacrylate, where n is the average molecular weight of the PEG chain.

5. The apparatus defined in claim 4 wherein the average molecular weight of the PEG chain is between about 50 and about 500.

6. The apparatus defined in claim 5 wherein the average molecular weight of the PEG chain is about 200.

7. The apparatus defined in claim 3 wherein said hydrogel polymer is a cross-linked network of hydrophilic monomers taken from the group consisting of unsaturated organic acid monomers, acrylic substituted alcohols, and acrylamides.

8. The apparatus defined in claim 2 wherein said chemical species is glucose.

9. An apparatus useful in detecting viability and metabolic activity of biological cells, comprising
    a substrate defining a microscopic chamber;
    at least one microcantilever connected to said substrate and extending into said chamber;
    a detector device operatively connected to said microcantilever for sensing a state of deformation thereof; and
    a layer of an environmentally sensitive hydrogel polymer provided on at least one surface of said microcantilever, said hydrogel polymer having a configuration changing in accordance with presence and absence of glucose, wherein said hydrogel polymer is a boronate-containing polymer complex that swells due to diffusion of ion species upon chemical responsiveness when in contact with glucose.

10. The apparatus defined in claim 1 wherein said environmental parameter is temperature.

11. The apparatus defined in claim 10 wherein said hydrogel polymer is poly(N-isopropylacrylamide) (PNIAAm).

12. The apparatus defined in claim 10 wherein said hydrogel polymer is obtained by polymerizing in an aqueous solution, N-alkyl acrylamide derivatives with acrylic acid, alkali metal salts of acrylic acid, or mixtures thereof, and diacetone acrylamide.

13. The apparatus defined in claim 1 wherein one of said valves is an inlet valve and the other of said valves is an outlet valve.

14. The apparatus defined in claim 13, further comprising a first microbore tube extending to said chamber for feeding said liquid sample to said chamber, also comprising a second microbore tube extending from said chamber for siphoning off of said liquid sample after testing has been completed, said inlet valve being disposed in operative relationship to said first microbore tube for controlling flow from said first microbore tube into said chamber, said outlet valve being disposed in operative relationship to said second microbore tube for controlling flow from said chamber into said second microbore tube.

15. A method for the detection of cell viability and metabolic activity, comprising:
   providing a solid state microbiological testing device including a microcantilever coated on at least one side with a hydrogel polymer sensitive to an environmental parameter modifiable by cellular metabolism, said microcantilever projecting into a chamber;
   feeding a liquid sample to said chamber, said liquid sample containing at least one biological cell;
   operating at least one inlet valve and at least one outlet valve to control fluid flow into and out of said chamber and to hold said liquid sample and concentrate said biological cell in said chamber; and
   automatically monitoring a state of deflection of said microcantilever to determine a change in a state of said microbiological parameter owing to metabolic activity of said biological cell.

16. The method defined in claim 15 wherein said environmental parameter is a chemical species, said hydrogel polymer being reactive with said species.

17. The method defined in claim 16 wherein said chemical species is the hydrogen ion, the state of deflection of said microcantilever being indicative of the pH of said liquid sample.

18. The method defined in claim 17 wherein said hydrogel polymer is a cross-linked network of hydrophilic monomers taken from the group consisting of methacrylic acids, acrylic acids, glycerolacrylate, glycerolmethacrylate, 2-hydroxyethylmethacrylate, 2-hydroxyethylacrylate, 2-(dimethylaminoethyl methacrylate, N-vinyl pyrrolidone, methacrylamide, and N,N-dimethylacrylamide poly(methacrylic acid) containing amounts of poly(ethylene glycol) n dimethacrylate, where n is the average molecular weight of the PEG chain.

19. The apparatus defined in claim 17 wherein said hydrogel polymer is a cross-linked network of hydrophilic monomers taken from the group consisting of unsaturated organic acid monomers, acrylic substituted alcohols, and acrylamides.

20. The method defined in claim 17 wherein said hydrogel polymer is a crosslinked poly(methacrylic acid) containing amounts of poly(ethylene glycol) n dimethacrylate, where n is the average molecular weight of the PEG chain.

21. The method defined in claim 16 wherein said chemical species is glucose.

22. The method defined in claim 21 wherein said hydrogel polymer is a boronate-containing polymer complex that swells due to diffusion of ion species upon chemical responsiveness when in contact with glucose.

23. The method defined in claim 15 wherein said environmental parameter is temperature.

24. The method defined in claim 23 wherein said hydrogel polymer is poly(N-isopropylacrylamide) (PNIAAm).

25. The method defined in claim 15 wherein said hydrogel polymer is obtained by polymerizing in an aqueous solution, N-alkyl acrylamide derivatives with acrylic acid, alkali metal salts of acrylic acid, or mixtures thereof, and diacetone acrylamide.

26. The method defined in claim 15 wherein the automatic monitoring of said state of deflection of said microcantilever includes a step taken from the group consisting of resistively sensing said state of deflection, optically sensing said state of deflection, and monitoring a resonance circuit including an element on said microcantilever.

27. The method defined in claim 15 wherein the feeding of said liquid sample to said chamber includes feeding said liquid sample through a first microbore tube extending to said chamber, the operating of said inlet valve effectuating a control of liquid flow through said first microbore tube, further comprising siphoning off said liquid sample through a second microbore tube after testing of said liquid sample has been completed, the operating of said outlet valve effectuating a control of liquid flow through said second microbore tube.

28. A method for the detection of cell viability and metabolic activity, comprising:
   providing a solid state microbiological testing device including a deformable cantilever element coated on at least one side with a hydrogel polymer sensitive to an environmental parameter modifiable by cellular metabolism, said cantilever element being in contact with a microscale-size chamber;
   feeding a liquid sample to said chamber, said liquid sample containing at least one biological cell;
   operating at least two valves to hold said liquid sample at least temporarily in said chamber, thereby performing a concentration of one or more biological cells in as small a volume as possible to achieve as high a cell concentration as possible in order to reduce the time to detection of the metabolic activity; and
   automatically monitoring a state of deformation of said cantilever element to determine a change in a state of said microbiological parameter owing to metabolic activity of said biological cell, said liquid sample being held in said chamber sufficiently long for metabolic activity of said biological cell to effect a detectable change in state of said microbiological parameter.

29. The method defined in claim 28 wherein the feeding of said liquid sample to said chamber includes feeding said liquid sample through a first microbore tube extending to said chamber, the operating of one of said valves effectuating a control of liquid flow through said first microbore tube, further comprising siphoning off said liquid sample through a second microbore tube after testing of said liquid sample has been completed, the operating of the other of said valves effectuating a control of liquid flow through said second microbore tube.

* * * * *